United States Patent
Jemielity et al.

(10) Patent No.: US 11,066,436 B2
(45) Date of Patent: Jul. 20, 2021

(54) 5'-PHOSPHOROTHIOLATE MRNA 5'-END (CAP) ANALOGS, MRNA COMPRISING THE SAME, METHOD OF OBTAINING AND USES THEREOF

(71) Applicant: Uniwersytet Warszawski, Warsaw (PL)

(72) Inventors: Jacek Jemielity, Warsaw (PL); Kaja Fac-Dąbrowska, Warsaw (PL); Błażej Wojtczak, Pabianice (PL); Marek Baranowski, Warsaw (PL); Anna Nowicka, Legionowo (PL); Joanna Kowalska, Warsaw (PL); Paweł Sikorski, Warsaw (PL); Marcin Warmiński, Warsaw (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 112 days.

(21) Appl. No.: 16/073,499

(22) PCT Filed: Jan. 27, 2017

(86) PCT No.: PCT/IB2017/050447
§ 371 (c)(1),
(2) Date: Jul. 27, 2018

(87) PCT Pub. No.: WO2017/130151
PCT Pub. Date: Aug. 3, 2017

(65) Prior Publication Data
US 2019/0300563 A1      Oct. 3, 2019

(30) Foreign Application Priority Data

Jan. 29, 2016   (PL) .......................... 415967

(51) Int. Cl.
| | | |
|---|---|---|
| *C07H 21/02* | (2006.01) | |
| *A61P 21/00* | (2006.01) | |
| *C07H 1/04* | (2006.01) | |
| *C07H 21/00* | (2006.01) | |

(52) U.S. Cl.
CPC .............. *C07H 21/02* (2013.01); *A61P 21/00* (2018.01); *C07H 1/04* (2013.01); *C07H 21/00* (2013.01)

(58) Field of Classification Search
None
See application file for complete search history.

(56) References Cited

FOREIGN PATENT DOCUMENTS

| EP | 2281579 A1 | 8/2009 |
|---|---|---|
| WO | 2008/157688 A2 | 6/2008 |
| WO | 2009/149253 A2 | 6/2009 |

OTHER PUBLICATIONS

Wotjtczak et al., J. Am. Chem. Soc. vol. 140:5987-5999, 2018.*
_International Search Report from PCT/IB2017/050447 dated May 18, 2017, 5 pages.
_IPRP from PCT/IB2017/050447 dated Jul. 31, 2018, 8 pages.
_Written Opinion from PCT/IB2017/050447 dated May 18, 2017, 7 pages.
Kowalska et al., (2008) "Synthesis and characterization of mRNA cap analogs containing phosphorothioate substitutions that bind tightly to eIF4E and are resistant to the decapping pyrophosphatase DcpS" RNA, vol. 14, pp. 1119-1131.
Wypijewska del Nogal et al. (2013) "Analysis of decapping scavenger cap complex using modified cap analogs reveals molecular determinants for efficient cap binding" FEBS Journal, vol. 280, pp. 6508-6527.

\* cited by examiner

*Primary Examiner* — Sean McGarry
(74) *Attorney, Agent, or Firm* — ALGM LLP; Harry J. Guttman

(57) ABSTRACT

The present invention relates to nucleotides, analogs of mRNA 5'-end (cap) containing sulfur atom at the position 5' of 7-methylguanosine nucleoside. The disclosed compounds are recognized (bound and non-hydrolyzed) by DcpS enzyme (Decapping Scavenger), and thus may find therapeutic use as inhibitors thereof. DcpS is cap-specific enzyme with pyrophosphatase activity, which was identified as a therapeutic target in the treatment of spinal muscular atrophy (SMA). Some of the compounds disclosed have additional modifications in the phosphate chain, which modulate their affinity for DcpS enzyme. The present invention also relates to mRNAs modified at the 5' end with mRNA 5'-end (cap) analogs containing 5'-phosphorothiolate moiety, which mRNAs have an increased stability and translational activity in cellular conditions, to a method of their preparation, their uses, and to a pharmaceutical formulation containing them, wherein $L^1$ and $L^2$ are independently selected from the group comprising O and S, wherein at least one of $L^1$ and $L^2$ is not O.

Formula 1

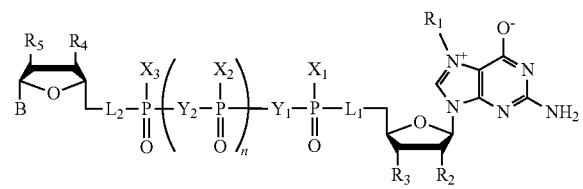

24 Claims, 9 Drawing Sheets

Specification includes a Sequence Listing.

Fig. 1. Synthesis of 5'-deoxy-5'-iodo-guanosine analogs

FIG. 2. SYNTHESIS OF 5'-DEOXY-5'-THIOGUANOSINE-5'-DIPHOSPHATE DERIVATIVES. PANEL A - SYNTHESIS OF GUANOSINE DERIVATIVE; PANEL B - SYNTHESIS OF 7-METHYLGUANOSINE DERIVATIVES

FIG. 3. SYNTHESIS OF 5'-THIOPHOSPHATE CAP ANALOGS VIA S-ALKYLATION. A - TERMINAL THIOPHOSPHATES USED IN ALKYLATION REACTION; WHICH ARE NOT CLAIMED, B - SCHEMES OF ALKYLATION REACTION BETWEEN 5'-DEOXY-5'-IODO-GUANOSINE (FIG. 1) AND TERMINAL THIOPHOSPHATES SHOWN IN A.

i) DBU, DMF, ROOM TEMPERATURE

FIG. 4. SYNTHESIS OF 5'-THIOPHOSPHATE CAP ANALOGS VIA IMIDAZOLIDES. A - COMPOUNDS USED IN THE METHOD, WHICH STRUCTURES HAVE NOT BEEN DISCLOSED BEFORE; B - FINAL COMPOUNDS SYNTHESIS IN REACTION BETWEEN TWO DIFFERENT ACTIVATED DERIVATIVE NO. 9 I 29.

FIG. 5. SUSCEPTIBILITY STUDIES OF A DINUCLEOTIDE SUBSTRATE (M7GPPPG) AND 5'-S MODIFIED CAP ANALOGS TO HYDROLYSIS MEDIATED BY THE DCPS ENZYME. PHOSPHATE TERMINOLOGY INDICATED ON THE STRUCTURE OF THE NATURAL DCPS ENZYME SUBSTRATE.

Fig. 6. The result of IC$_{50}$ determination for compounds: m$^7$GSpp$_s$pSG D2, m$^7$GSpp, m$^7$GDP and RG3039.

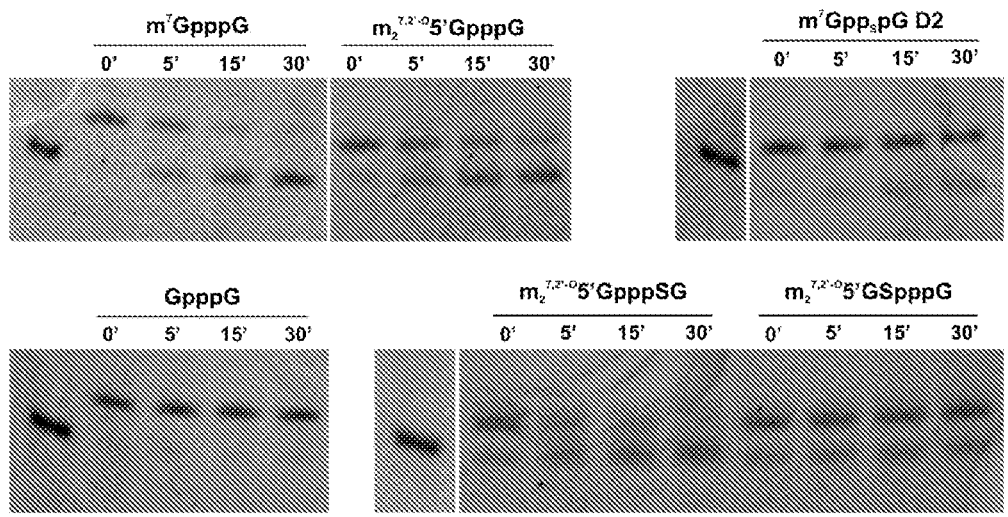
Fig. 8. Susceptibility to Dcp1/2 enzyme activity.
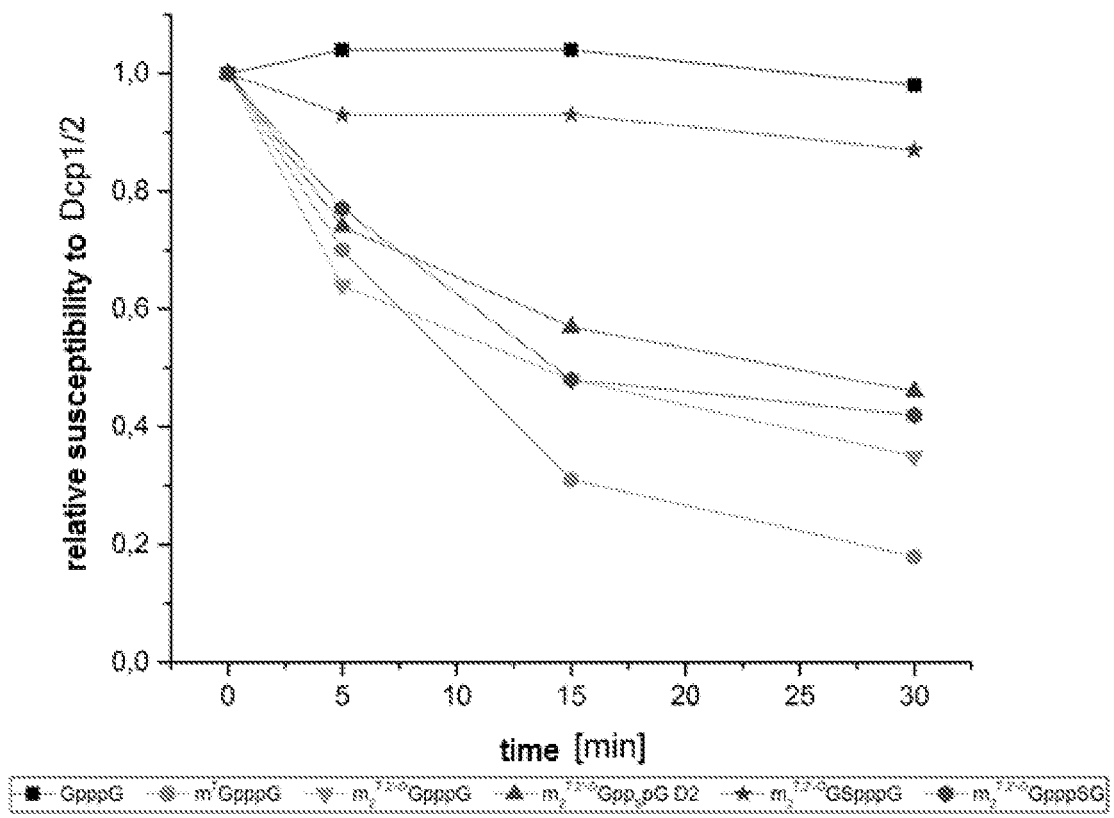
Fig. 9. Relative susceptibility to Dcp1/2 enzyme activity

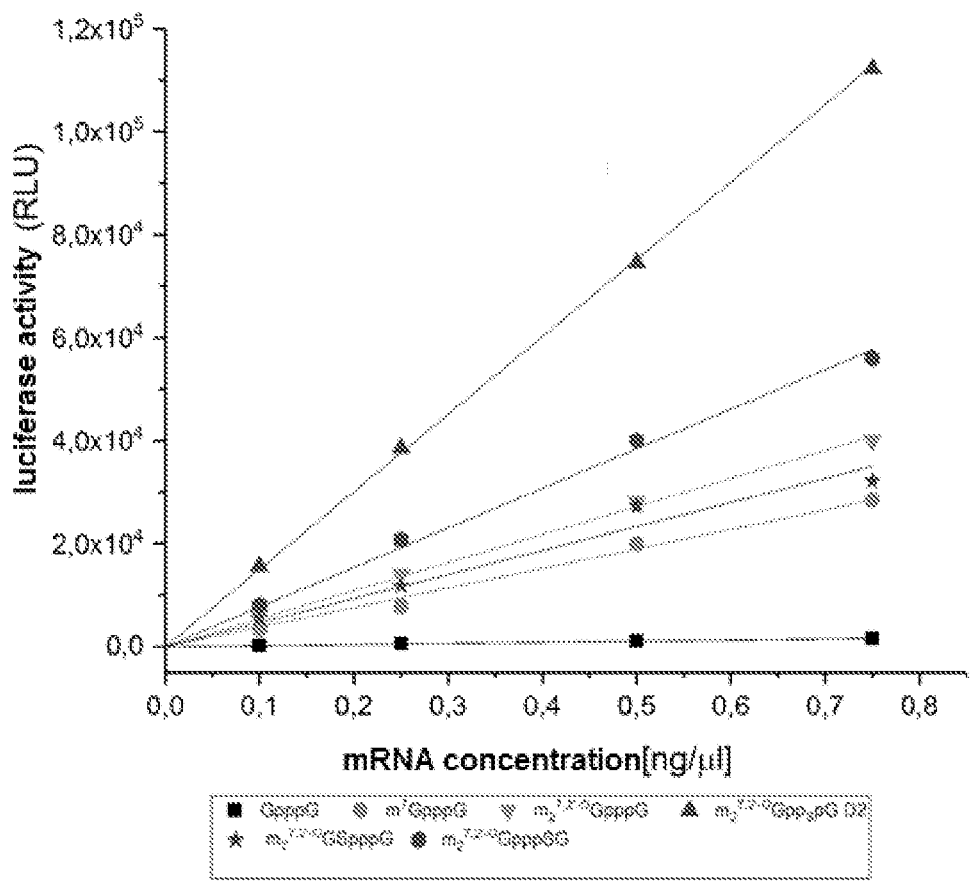
Fig. 10. Relative translational efficiency.
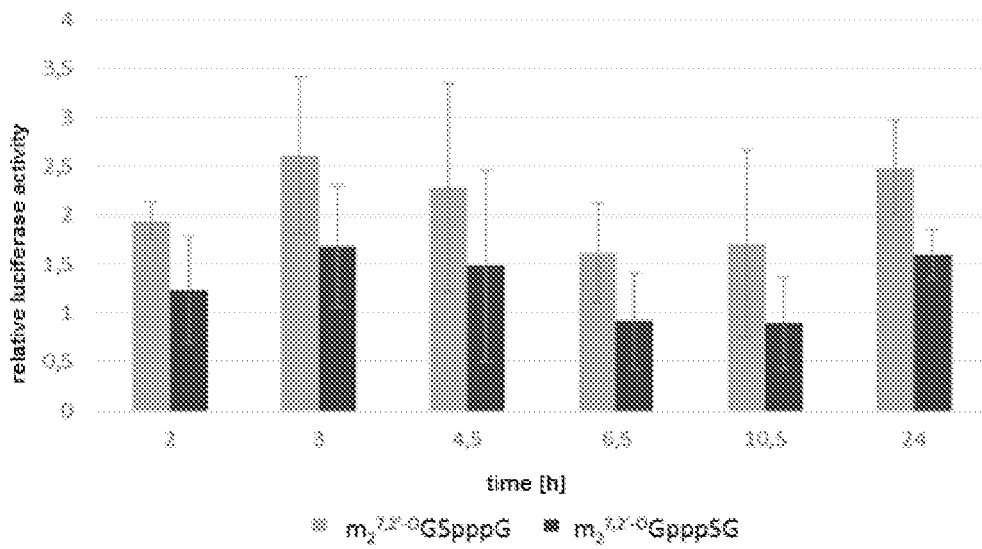
Fig. 11. Relative translational efficiency in HeLa cells

SEQUENCE LISTING

```
<160> NUMBER OF SEQ ID NOS: 7

<210> SEQ ID NO 1
<211> LENGTH: 57
<212> TYPE: DNA
<213> ORGANISM: artificial
<220> FEATURE:
<223> OTHER INFORMATION: Oligonucleotide 1

<400> SEQUENCE: 1
atacgattta ggtgacacta tagaagaagc gggcatgcgg ccagccatag ccgatca        57

<210> SEQ ID NO 2
<211> LENGTH: 57
<212> TYPE: DNA
<213> ORGANISM: artificial
<220> FEATURE:
<223> OTHER INFORMATION: Oligonucleotide 2

<400> SEQUENCE: 2
tgatcggcta tggctggccg catgcccgct tcttctatag tgtcacctaa atcgtat        57

<210> SEQ ID NO 3
<211> LENGTH: 19
<212> TYPE: DNA
<213> ORGANISM: artificial
<220> FEATURE:
<223> OTHER INFORMATION: SP6 polymerase promotor seq

<400> SEQUENCE: 3
atttaggtga cactataga                                                  19

<210> SEQ ID NO 4
<211> LENGTH: 35
<212> TYPE: RNA
<213> ORGANISM: artificial
```

```
<220> FEATURE:
<223> OTHER INFORMATION: Short RNA transcript

<400> SEQUENCE: 4
gaagaagcgg gcaugcggcc agccauagcc gauca                              35

<210> SEQ ID NO 5
<211> LENGTH: 35
<212> TYPE: DNA
<213> ORGANISM: artificial
<220> FEATURE:
<223> OTHER INFORMATION: DNazym 10-23

<400> SEQUENCE: 5
tgatcggcta ggctagctac aacgaggctg gccgc                              35

<210> SEQ ID NO 6
<211> LENGTH: 40
<212> TYPE: DNA
<213> ORGANISM: artificial
<220> FEATURE:
<223> OTHER INFORMATION: Oligonucleotide 3

<400> SEQUENCE: 6
atttaggtga cactatagaa cagatctcga gctcaagctt                         40

<210> SEQ ID NO 7
<211> LENGTH: 23
<212> TYPE: DNA
<213> ORGANISM: artificial
<220> FEATURE:
<223> OTHER INFORMATION: Oligonucleotide 4

<400> SEQUENCE: 7
gtttaaacat ttaaatgcaa tga                                           23
```

5'-PHOSPHOROTHIOLATE MRNA 5'-END (CAP) ANALOGS, MRNA COMPRISING THE SAME, METHOD OF OBTAINING AND USES THEREOF

TECHNICAL FIELD

The present invention relates to analogs of mRNA 5'-end (cap) containing 5'-phosphorothiolate moiety, a method of their preparation, intermediates and uses thereof.

5'-phosphorothiolate cap analogs are used as DcpS enzyme inhibitors which enables their application as a medicine, especially for spinal muscular atrophy (SMA) treatment. The present invention also relates to mRNA modified at the 5' end with mRNA 5'-end (cap) analogs containing 5'-phosphorothiolate moiety according to the invention, wherein the modification aims at obtaining of mRNA transcripts with an increased stability and translational activity under cellular conditions. Transcripts with such properties are applicable in novel gene therapies based on mRNA.

BACKGROUND ART

Chemically derived mRNA 5'-end analogs have a variety of uses, and modifications implemented within this structure may significantly modify the biological properties of these compounds (Ziemniak, Strenkowska et al., 2013). Among the various applications of cap analogs, the most frequent involve their use as low-molecular inhibitors of cap-dependent processes for therapeutic purposes (e.g., inhibition of DcpS enzyme—spinal muscular atrophy therapy). On the other hand, suitably modified dinucleotide cap analogs are used to modify messenger mRNA by co-transcription in vitro, in order to obtain transcripts with improved stability and translational activity under cellular conditions. Transcripts with such properties are being increasingly studied in the context of novel gene therapies based on mRNA. In the latter case, cap structure resistance to another decapping enzyme, Dcp2, is a key issue.

DcpS enzyme (Decapping Scavenger) is an enzyme involved in mRNA degradation process in eukaryotes. There are two main pathways of mRNA degradation in eukaryotic cells, 5'→3' degradation and 3'→5' degradation (Rydzik, Lukaszewicz et al., 2009). Both degradation pathways are initiated by deadenylation. The degradation in direction 5'→3' is followed by mRNA decapping as a result of cutting of the bond between $\alpha$ and $\beta$ phosphates, and degradation by 5'-exonuclease. 3'→5' degradation involves mRNA degradation by exosome starting from the 3'-end. Such degradation results in a release of dinucleotide cap residues or cap-ended short oligonucleotides, which are then degraded by DcpS enzyme. DcpS belongs to HIT family pyrophosphatases and hydrolyzes the cap between $\gamma$ and $\beta$ phosphates releasing 7-methylguanosine 5'-monophosphate ($m^7GMP$) and a second product, which is accordingly a nucleoside 5'-diphosphate or a short oligonucleotide. Longer cap-ended mRNA are not substrates for DcpS. Also 7-methylguanosine 5'-diphosphate ($m^7GDP$), which is a product of 5'→3' mRNA degradation, is not a substrate for DcpS. An activity of DcpS enzyme is considered vital for cell homeostasis, since unnecessary cap residues released from mRNA during 3'→5' degradation could adversely affect other cap-dependent cellular processes. DcpS is located both in the cytoplasm and the nucleus, where it may be involved in splicing regulation (Shen, Liu et al., 2008). Therefore, it was suggested that DcpS role in the cell goes beyond its well characterized functions in 3'→5' mRNA degradation (Bail and Kiledjian 2008).

It was reported in 2008 that DcpS inhibition can provide a therapeutic effect in spinal muscular atrophy. SMA is a common neurodegenerative disease occurring on average once every 6000 births (Akagi and Campbell 1962). It is caused by low levels of SMN protein (Survival Motor Neuron), which is encoded by SMN genes. Two SMN genes, i.e., SMN1 and SMN2, are present in humans. The main difference between them is a sequence change in exon 7, which affects pre-mRNA splicing. As a result, an expression of SMN1 gene leads to a stable and functional protein, while the protein expressed from SMN2 is shortened. Mutations in both copies of SMN1 gene, including deletions, conversions to SMN2-like gene and point mutations, result in SMA disease. People who have only one defective SMN1 copy are SMA carriers, but do not show any symptoms of the disease.

Homologous SMN2 gene cannot provide sufficient amounts of functional SMN protein, but it was observed that higher number of SMN2 gene copies is accompanied by a more benign course of the disease. Therefore, it is believed that compounds which increase an amount of protein encoded by the SMN2 gene in a cell can be therapeutics against SMA. It was found that some 5-substituted quinazolines may increase SMN2 gene expression even twofold (Akagi and Campbell, 1962). Trying to unravel the molecular mechanism underlying this activation, in another study using radioactive labeling, authors identified DcpS as the protein binding 5-substituted quinazoline.

These experiments allowed to identify DcpS as a therapeutic target in SMA treatment.

Further studies indicated that various C5-substituted quinazolines are potent inhibitors of the DcpS enzyme (already at nanomolar concentrations), and that the inhibitor potential is correlated with the level of SMN2 gene promoter activation. The therapeutic potential of these compounds was then demonstrated in vivo in a mouse model (Butchbach, Singh et al., 2010). It was reported recently that one of the DcpS inhibitors, RG3039 compound, improves motor function in mice with SMA (Van Meerbeke, Gibbs et al,).

Despite ongoing preclinical and clinical trials, there is still no effective treatment of SMA, therefore, there is a continuing need for new compounds with therapeutic potential.

Dinucleotide cap analogs with modifications in triphosphate bridge and 7-methylguanosine ribose may be used for the synthesis of capped RNA molecules in vitro. The method is useful since it allows to obtain RNA molecules with improved biological properties, in particular, an increased translational activity and prolonged half-life in cells (Grudzien, Kalek et al., 2006). These both features cause, that a significantly higher amount of protein is obtained while utilizing the same amount of mRNA. This may find a wide range of applications both in research, and for commercial production of peptides and proteins, including therapeutic applications, e.g. in cancer immunotherapy (Sahin, Kariko et al., 2014).

The most common method used to obtain capped mRNA in vitro, is the synthesis of mRNA on DNA template using bacterial or bacteriophage RNA polymerase in the presence of all four ribonucleoside triphosphates and a cap dinucleotide such as ($m^7GpppG$). Polymerase initiates the transcription by nucleophilic attack of 3'-OH of Guo moiety in $m^7GpppG$ on alpha-phosphate of the next transcribed nucleoside triphosphate, resulting in $m^7GpppGpN$ as an initial product (Contreras and Fiers 1981, Konarska, Padgett et al., 1984).

The amount of protein produced by a synthetic mRNA introduced to a culture of mammalian cells is limited by mRNA degradation in cellular conditions. In vivo mRNA degradation is mainly initiated by cap removal from the 5'-end of mRNA by a specific pyrophosphatase Dcp1/Dcp2 which cleaves the bond between the alpha and beta phosphates (Mildvan, Xia et al., 2005). Dcp2 enzyme, which forms a complex with a regulatory protein Dcp1, is responsible for cleaving off the cap structure from the full length transcripts or from at least 20 nucleotide fragments thereof (Lykke-Andersen 2002). The Dcp1/Dcp2 complex plays a key role in gene expression regulation. Making the mRNA transcripts within the cap resistant to this enzyme activity leads to an increased expression of the protein encoded by such modified mRNA (Ziemniak, Strenkowska et al., 2013). When the modification does not simultaneously impair interactions with a translation initiating factor, then this leads to an increased mRNA translational activity. mRNAs having such properties are desirable for therapeutic applications including cancer immunotherapy (Kuhn, Diken et al., 2010), stem cells reprogramming (Warren, Manos et al., 2010) or supplementation of proteins formed in the cells in a defected form or in insufficient quantities. Modifications in a triphosphate bridge of a cap structure are known in literature, increasing the resistance to Dcp2 enzyme. These include, inter alia, analogs where oxygen atoms at alpha-beta bridge position were substituted with a methylene group, analogs, where the non-bridge oxygen at beta position was replaced by a sulfur atom or a boranophosphate group. In the case of the methylene analog, an increased mRNA stability did not result in an increase in the efficiency of protein synthesis in cells, which was probably due to decreased affinity to eIF4E protein (Grudzien, Kalek et al., 2006). In the case of non-bridge modifications in beta position, an increased resistance to Dcp2 and increased affinity for eIF4E resulted in an increased translational activity of such modified mRNA in the cells (Grudzien-Nogalska, Jemielity et al., 2007) (Kowalska, Wypijewska del Nogal et al., 2014). A common feature of all cap analogs that upon incorporation into mRNA demonstrated reduced susceptibility to degradation by Dcp2 was the localization of the modification near the site of cap cleavage by enzyme, i.e., alpha-beta position in triphosphate bridge.

DISCLOSURE OF INVENTION

Taking into account the described state of the art, the aim of the present invention is to overcome the indicated disadvantages and to provide a new class of nucleotide mRNA 5'-end analogs affecting DcpS activity, their uses, including in SMA treatment, as well as methods for their synthesis.

Another aim of the invention is to provide mRNA modified at the 5' end with mRNA 5'-end (cap) analogs containing 5'-phosphorothiolate moiety, thereby increasing mRNA stability and biosynthesis efficiency of protein encoded by that mRNA in the cells. Another aim of the invention is to provide mRNA modified at the 5' end with mRNA 5'-end (cap) analogs containing 5'-phosphorothiolate moiety, which transcripts are intended for use as a medicine, including for use in novel gene therapies based on mRNA.

The present invention relates to a novel class of nucleotide mRNA 5'-end analogs. The new analogs contain sulfur atom at the position of 5'-nucleoside, i.e., at least one of oxygen atoms in position 5' was replaced by a sulfur atom. We surprisingly discovered that the new analogs containing the modification with sulfur atom in position 5' from the side of 7-methylguanosine are resistant to hydrolytic activity of DcpS enzyme, and are inhibitors of DcpS enzyme, thus affecting the expression of SMN proteins, which is of therapeutic relevance in SMA treatment. Such compounds being stable against the activity of DcpS and/or affecting DcpS activity will also be used in the regulation of mRNA degradation as well as splicing modulation and regulation. The following analogs were found to be particularly preferred from the viewpoint of inhibitory properties: $m^7GSpppG$ (no. 24), $m^7GSpppSG$ (no. 32), $m^7GSpp_spG$ D1 (no. 30), $m^7GSpp_spG$ D2 (no. 31), $m^7GSpp_spSG$ D1 (no. 33), $m^7GSpp_spSG$ D2 (no. 34), and the most preferred was $m^7GSpp_spSG$ D2 (no. 34). Equally beneficial were analogs $m^7GSpp$ (no. 12), $m^7GSppG$ (no. 23), $m^7GSppCH_2pG$ (no. 25), $m^{7,2'O}GSpppG$ (no. 26), $m^7GpCH_2ppSG$ (no. 37).

The present invention also relates to mRNA modified at the 5' end with mRNA 5'-end (cap) analogs containing 5'-phosphorothiolate moiety, thereby increasing mRNA stability and biosynthesis efficiency of protein encoded by that mRNA in the cells. The present invention also relates to mRNA modified at the 5' end with mRNA 5'-end (cap) analogs containing 5'-phosphorothiolate moiety, which modified mRNA are intended for use as a medicine, including for the use in novel gene therapies based on mRNA.

Surprisingly, the inventors found that the new analogs according to the present invention containing the modifications with sulfur atom in position 5' from the side of 7-methylguanosine after incorporation into mRNA by an in vitro transcription method become resistant to the hydrolytic activity of enzyme Dcp1/2, and thus they affect the stability of mRNA and the efficiency of biosynthesis of protein encoded by this mRNA in a cell, including HeLa cell line. This is the first time when a modification located away from the site of triphosphate bridge cleavage in the cap by Dcp1/2 makes the cap structure resistant to the process of its removal, leading to an increased half-life of mRNA. This unexpected finding is of significant therapeutic importance in gene therapies involving an expression of the desired protein on the basis of the supplied synthetic mRNA, as is the case of specific activation of the immune system in cancer immunotherapy. Thus modified mRNA transcripts, for example encoding a protein characteristic for a given cancer type, may be used to activate the immune system against cancer cells containing this specific antigen. The following analogs were found to be particularly preferred from the viewpoint of translational properties of the modified mRNA: $m^7GSpppG$ (no. 24), $m^{7,2'O}GSpppG$ (no. 26), $m^7GSpppSG$ (no. 32), $m^7GSpp_spG$ D1 (no. 30), $m^7GSpp_spG$ D2 (no. 31), $m^7GSpp_spSG$ D1 (no. 33), $m^7GSpp_spSG$ D2 (no. 34), and the most preferred was $m^{7,2'O}GSpppG$ (no 26).

The present invention relates a 5'-phosphorothiolate cap analog according to formula 1

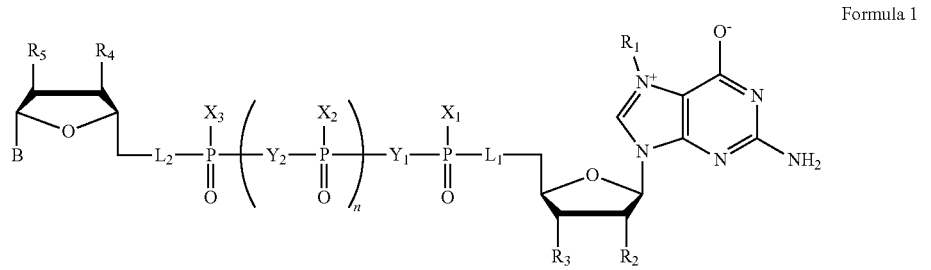

Formula 1 wherein
$L^1$ and $L^2$ are independently selected from the group comprising O and S, wherein at least one of $L_1$ and $L_2$ is not O;
n=0, 1, or 2;
$X_1$, $X_2$, $X_3$ are independently selected from the group comprising O, S;
$R^1$ is selected from the group comprising $CH_3$, $C_2H_5$, $CH_2Ph$, alkyl or substituted alkyl;
$R^2$ and $R^3$ are independently selected from the group comprising H, OH, $OCH_3$, $OC_2H_5$, —COOH, $CH_2COOH$, $N_3$, $CH_2N_3$, alkyl, alkenyl, or alkynyl;
$R^4$ and $R^5$ are independently selected from the group comprising H, OH, $OCH_3$, $OC_2H_5$, —COOH, $CH_2COOH$, $N_3$, $CH_2N_3$, alkyl, alkenyl, or alkynyl;
$Y_1$, $Y_2$ are independently selected from the group comprising $CH_2$, CHCl, $CCl_2$, $CF_2$, CHF, NH, O;
and B is a group according to formula 3, 4, 5, 6, or 7

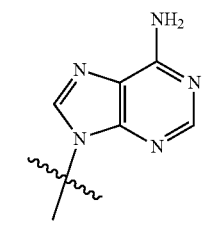

formula 3

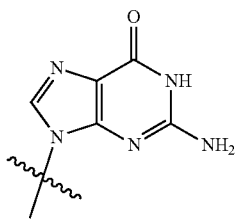

formula 4

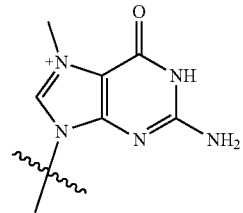

formula 5

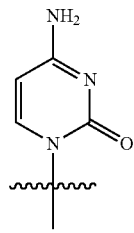

formula 6

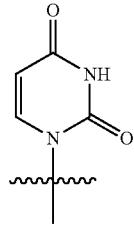

formula 7

A preferred 5'-phosphorothiolate cap analog is selected from the group consisting of:

| No | Compound | Structural formula | Chemical name |
|---|---|---|---|
| 21 | m⁷GppSG | | P1-(7-methyl-guanosin-5'-yl)-P2-(5'-deoxy-5'-thioguanosin-5'-yl) diphosphate |

-continued

| No | Compound | Structural formula | Chemical name |
|----|----------|--------------------|---------------|
| 22 | m⁷GpppSG | | P1-(7-methyl-guanosin-5'-yl)-P3-(5'-deoxy-5'-thioguanosin-5'-yl) triphosphate |
| 23 | m⁷GSppG | | P1-(7-methyl-5'-deoxy-5'-thioguanosin-5'-yl)-P2-guanosin-5'-yl diphosphate |
| 24 | m⁷GSpppG | | P1-(7-methyl-5'-deoxy-5'-thiogunosin-5'-yl)-P3-guanosin-5'-yl triphosphate |
| 25 | m⁷GSppCH₂pG | | P1-(7-methyl-5'-deoxy-5'-thioguanosin-5'-yl)-P3-guanosin-5'-yl 2,3-methylenotriphosphate |
| 26 | m⁷,²'ᴼGSpppG | | P1-(2'-O-methyl-7-methyl-5'-deoxy-5'-thioguanosin-5'-yl)-P3-guanosin-5'-yl triphosphate |
| 30 | m⁷GSpp$_s$pG D1 | | P1-(7-methyl-5'-deoxy-5'-thioguanosin-5'-yl)-P3-guanosin-5'-yl-thiotriphosphate D1 |

-continued

| No | Compound | Structural formula | Chemical name |
|---|---|---|---|
| 31 | m⁷GSpp$_s$pG D2 | | P1-(7-methyl-5'-deoxy-5'-thioguanosin-5'-yl)-P3-guanosin-5'-yl 2-thiotriphosphate D2 |
| 32 | m⁷GSpppSG | | P1-(7-methyl-5'-deoxy-5'-thioguanosin-5'-yl)-P3-(5'-deoxy-5'-thioguanosin-5'-yl) triphosphate |
| 33 | m⁷GSpp$_s$pSG D1 | | P1-(7-methyl-5'-deoxy-5'-thioguanosin-5'-yl)-P3-(5'-deoxy-5'-thioguanosin-5'-yl) 2-tiotriphosphate D1 |
| 34 | m⁷GSpp$_s$pSG D2 | | P1-(7-methyl-5'-deoxy-5'-thioguanosin-5'-yl)-P3-(5'-deoxy-5'-thioguanosin-5'-yl) 2-thiotriphosphate D2 |
| 35 | m⁷Gpp$_s$pSG D1 | | P1-(7-methyl-guanosin-5'-yl)-P3-(5'-deoxy-5'-thioguanosin-5'-yl) 2-tiotriphosphate D1 |
| 36 | m⁷Gpp$_s$pSG D2 | | P1-(7-methyl-guanosin-5'-yl)-P3-(5'-deoxy-5'-thioguanosin-5'-yl) 2-thiotrifphosphate D2 |

-continued

| No | Compound | Structural formula | Chemical name |
|---|---|---|---|
| 37 | m⁷GpCH₂ppSG | | P1-(7-methyl-5'-deoxy-5'-thioguanosin-5'-yl)-P3-guanosin-5'-yl 1,2-methylenotriphosphate |
| 38 | m⁷,²'ᴼGpppSG | | P1-(2'-O-methyl-7-methyl-guanosin-5'-yl)-P3-(5'-deoxy-5'-thioguanosin-5'-yl) triphosphate |

Even more preferred 5'-phosphorothiolate cap analog compound is selected from the group consisting of:

| No | Compound | Structural formula | Chemical name |
|---|---|---|---|
| 23 | m⁷GSppG | | P1-(7-methyl-5'-deoxy-5'-thioguanosin-5'-yl)-P2-guanosin-5'-yl diphosphate |
| 24 | m⁷GSpppG | | P1-(7-methyl-5'-deoxy-5'-thioguanosin-5'-yl)-P3-guanosin-5'-yl triphosphate |
| 25 | m⁷GSppCH₂pG | | P1-(7-methyl-5'-deoxy-5'-thioguanosin-5'-yl)-P3-guanosin-5'-yl 2,3-methylenotriphosphate |
| 26 | m⁷,²'ᴼGSpppG | | P1-(2'-O-methyl-7-methyl-5'-deoxy-5'-thioguanosin-5'-yl)-P3-guanosin-5'-yl triphosphate |

| No | Compound | Structural formula | Chemical name |
|---|---|---|---|
| 30 | m⁷GSpp$_s$pG D1 | | P1-(7-methyl-5'-deoxy-5'-thioguanosin-5'-yl)-P3-guanosin-5'-yl 2-triphosphate D1 |
| 31 | m⁷GSpp$_s$pG D2 | | P1-(7-methyl-5'-deoxy-5'-thioguanosin-5'-yl)-P3-guanosin-5'-yl 2-thiotriphosphate D2 |
| 32 | m⁷GSpppSG | | P1-(7-methyl-5'-deoxy-5'-thioguanosin-5'-yl)-P3-(5'-deoxy-5'-thioguanosin-5'-yl) triphosphate |
| 33 | m⁷GSpp$_s$pSG D1 | | P1-(7-methyl-5'-deoxy-5'-thioguanosin-5'-yl)-P3-(5'-deoxy-5'-thioguanosin-5'-yl) 2-thiotriphosphate D1 |
| 34 | m⁷GSpp$_s$pSG D2 | | P1-(7-methyl-5'-deoxy-5'-thioguanosin-5'-yl)-P3-(5'-deoxy-5'-thioguanosin-5'-yl) 2-thiotriphosphate D2 |
| 37 | m⁷GpCH$_2$ppSG | | P1-(7-methyl-5'-deoxy-5'-thioguanosin-5'-yl)-P3-guanosin-5'-yl 1,2-methylenethiotriphosphate |

The invention also relates to a 5'-phosphorothiolate analog according to formula 2

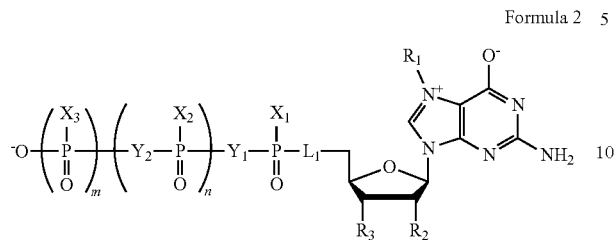

Formula 2 wherein
m=0, 1
n=0, 1, or 2;
$L^1$ is S
$X_1$, $X_2$, $X_3$ are independently selected from the group comprising O, S;
$R^1$ is selected from the group comprising $CH_3$, $C_2H_5$, $CH_2Ph$, alkyl, or substituted alkyl;
$R^2$ and $R^3$ are independently selected from the group comprising H, OH, $OCH_3$, $OC_2H_5$, —COOH, $N_3$, alkyl, or substituted alkyl;
$Y_1$, $Y_2$ are independently selected from the group comprising $CH_2$, CHCl, $CCl_2$, CHF, $CF_2$, NH and O;

A preferred 5'-phosphorothiolate analog is 7-methylguanosine 5'-deoxy-5'-thioguanosine 5'-diphosphorothiolate of formula 13 below

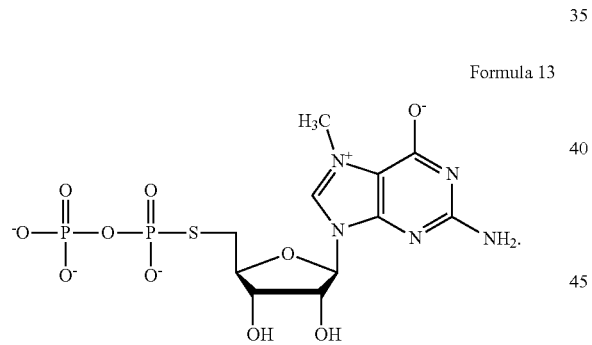

Formula 13

The invention also relates to the 5'-phosphorothiolate cap analog according to the invention for use as a medicament.

The invention also relates to the 5'-phosphorothiolate cap analog according to the invention for use as a medicament for treatment of spinal muscular atrophy (SMA) and/or alleviation of symptoms of SMA.

The invention also relates to a use of the 5'-phosphorothiolate cap analog according to the invention in preparation of a medicament.

The invention also relates to a use of the 5'-phosphorothiolate cap analog according to the invention in preparation of a medicament for treatment of spinal muscular atrophy (SMA) and/or alleviation of symptoms of SMA.

The present invention also relates to a use of the 5'-phosphorothiolate cap analog according to the invention as a regulator of DcpS activity, preferably as an inhibitor of DcpS enzyme activity, more preferably hDcpS.

The invention also relates to a use of the 5'-phosphorothiolate cap analog according to the invention in regulation of mRNA degradation and/or in regulation of mRNA splicing.

The invention additionally relates to analogs of 5'-deoxy-5'-iodoguanosine having structures according to formulas 10, 11, and 12 shown below.

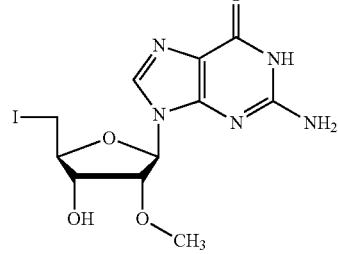

formula 10

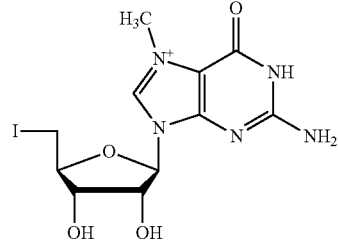

formula 11

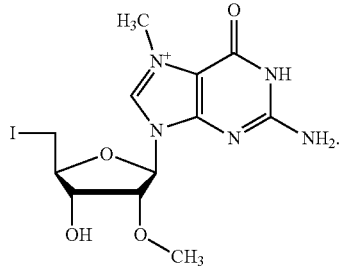

formula 12

The present invention additionally relates to a method of preparation of compound according to formula 1, said method comprising: steps wherein a 5'-iodonucleoside according to formula 8

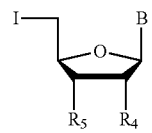

Formula 8 wherein
$R^4$ and $R^5$ are independently selected from the group comprising H, OH, $OCH_3$, $OC_2H_5$, —COOH, $N_3$, alkyl, or substituted alkyl;
and B is a group according to formula 3, 4, 5, 6, or 7

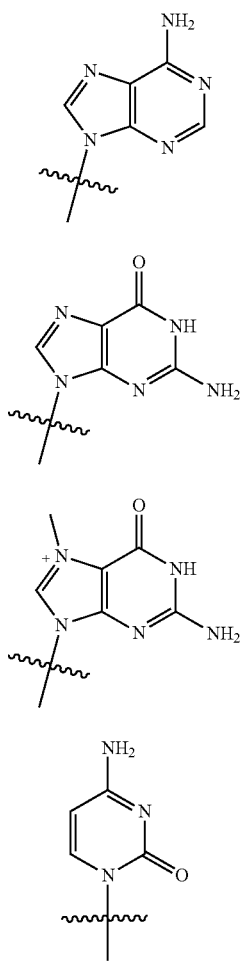

formula 3

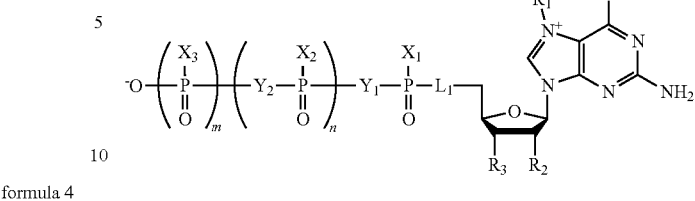

wherein m=0, 1 n=0, 1, or 2;

$L^1$ is O or S;

$X_1$, $X_2$, $X_3$ are independently selected from the group comprising O, S;

$R^1$ is selected from the group comprising $CH_3$, $C_2H_5$, $CH_2Ph$, alkyl, or substituted alkyl $R^2$ and $R^3$ are independently selected from the group comprising H, OH, $OCH_3$, $OC_2H_5$, —COOH, $N_3$, alkyl, or substituted alkyl;

$Y_1$ and $Y_2$ are independently selected from the group comprising $CH_2$, CHCl, $CCl_2$, CHF, $CF_2$, NH, and O;

wherein if n=0 and m=1 then $X_3$ is S, and $X_1$ is O;

if n=1 and m=0 then $X_2$ is S; and $X_1$ is O;

if n=1 and m=1 then $X_3$ is S; and $X_1$, $X_2$ are O to form a 5'-phosphorothiolate cap analog according to formula 1

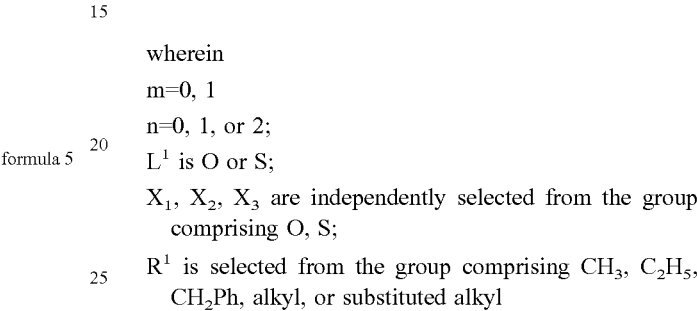

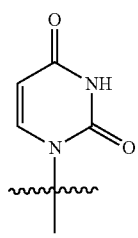

-continued formula 7 is reacted with a 5'-phosphorothiolate analog according to formula 2 comprising a terminal thiophosphate moiety

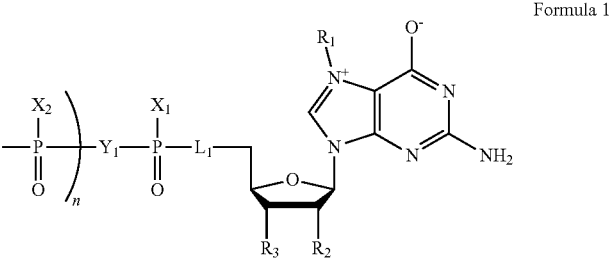

wherein $L^1$ and $L^2$ are independently selected from the group comprising O and S, wherein at least one of $L_1$ and $L_2$ is not O;

n=0, 1, or 2;

$X_1$, $X_2$, $X_3$ are independently selected from the group comprising O, S;

$R^1$ is selected from the group comprising $CH_3$, $C_2H_5$, $CH_2Ph$, alkyl or substituted alkyl;

$R^2$ and $R^3$ are independently selected from the group comprising H, OH, $OCH_3$, $OC_2H_5$, —COOH, $CH_2COOH$, $N_3$, $CH_2N_3$, alkyl, alkenyl, or alkynyl;

R[4] and R[5] are independently selected from the group comprising H, OH, $OCH_3$, $OC_2H_5$, —COOH, $CH_2COOH$, $N_3$, $CH_2N_3$, alkyl, alkenyl, or alkynyl;

$Y_1$, $Y_2$ are independently selected from the group comprising $CH_2$, CHCl, $CCl_2$, $CF_2$, CHF, NH, O;

and B is a group according to formula 3, 4, 5, 6 or 7 formula 3
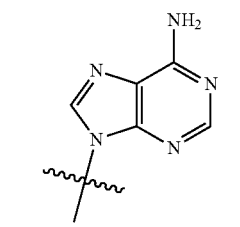

formula 4
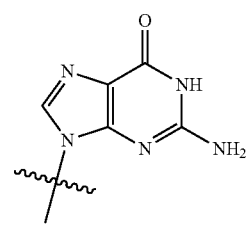

formula 5
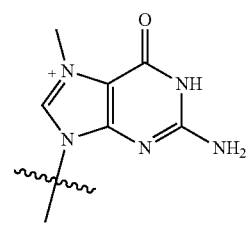

formula 6
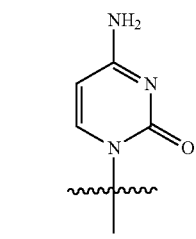

formula 7
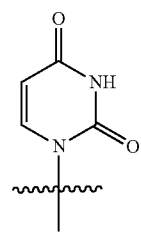

Preferably, the above mentioned synthesis method comprises using equimolar amounts of the compound according to formula 2, the compound according to formula 8 and DBU (1,8-diazabicyclo(5.4.0)undec-7-ene) as a base.

The invention also relates to a method of preparation of 5'-phosphorothiolate analog according to formula 2a, wherein an imidazolide derivative according to formula 9.

Formula 9
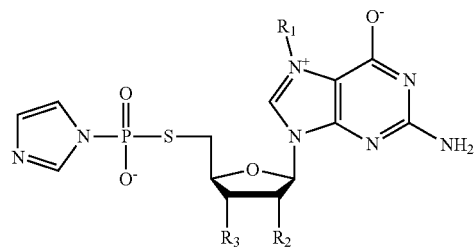

wherein
R[1] is selected from the group comprising $CH_3$, $C_2H_5$, $CH_2Ph$, alkyl, or substituted alkyl;
R[2] i R[3] are independently selected from the group comprising H, OH, $OCH_3$, $OC_2H_5$, —COOH, $N_3$, alkyl, or substituted alkyl;
is reacted with a triethylammonium phosphate salt or sodium thiophosphate to form a 5'-phosphorothiolate analog according to formula 2a Formula 2a
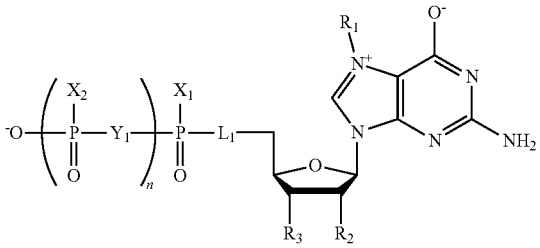

wherein
n=0, 1, or 2;
L[1] is O or S;
$X_1$ and $X_2$ are independently selected from a group comprising O, S;
R[1] is selected from a group comprising $CH_3$, $C_2H_5$, $CH_2Ph$, alkyl, or substituted alkyl;
R[2] and R[3] are independently selected from a group comprising H, OH, $OCH_3$, $OC_2H_5$, —COOH, $N_3$, alkyl, or substituted alkyl;
Y[1] is independently selected from a group comprising $CH_2$, CHCl, $CCl_2$, CHF, $CF_2$, NH, or O.

The invention also relates to a method of preparation of the compound according to formula 1, said method comprising steps wherein:
an imidazolide derivative according to formula 9

Formula 9
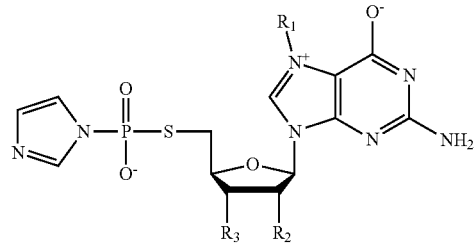

wherein
R$^1$ is selected from a group comprising CH$_3$, C$_2$H$_5$, CH$_2$Ph, alkyl, or substituted alkyl;
R$^2$ and R$^3$ are independently selected from a group comprising H, OH, OCH$_3$, OC$_2$H$_5$, —COOH, N$_3$, alkyl, or substituted alkyl;
is reacted with a 5'-phosphorothiolate analog according to formula 2a comprising a terminal thiophosphate moiety

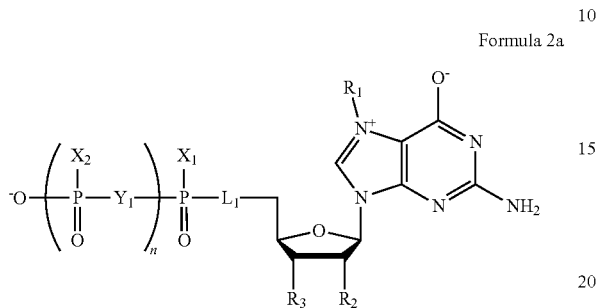

Formula 2a wherein
n=1
L$^1$ is O or S;
X$_1$ and X$_2$ are independently selected from a group comprising O, S;
R$^1$ is selected from a group comprising CH$_3$, C$_2$H$_5$, CH$_2$Ph, alkyl, or substituted alkyl;
R$^2$ and R$^3$ are independently selected from a group comprising H, OH, OCH$_3$, OC$_2$H$_5$, —COOH, N$_3$, alkyl, or substituted alkyl;
Y$_1$ is independently selected from a group comprising CH$_2$, CHCl, CCl$_2$, CHF, CF$_2$, NH, or O.
to form a 5'-phosphorothiolate cap analog according to formula 1

Y$_1$, Y$_2$ are independently selected from the group comprising CH$_2$, CHCl, CCl$_2$, CF$_2$, CHF, NH, O;
and B is a group according to formula 3, 4, 5, 6 or 7

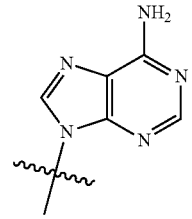

formula 3

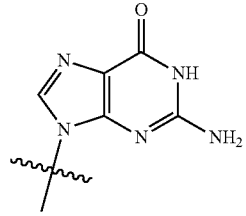

formula 4

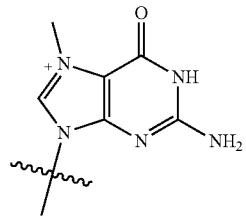

formula 5

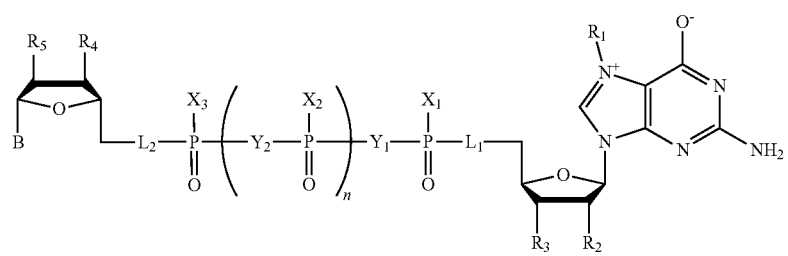

Formula 1 wherein
L$^1$ and L$^2$ are independently selected from the group comprising O and S, wherein at least one of L$_1$ and L$_2$ is not O;
n=0, 1, or 2;
X$_1$, X$_2$, X$_3$ are independently selected from the group comprising O, S;
R$^1$ is selected from the group comprising CH$_3$, C$_2$H$_5$, CH$_2$Ph, alkyl or substituted alkyl;
R$^2$ and R$^3$ are independently selected from the group comprising H, OH, OCH$_3$, OC$_2$H$_5$, —COOH, CH$_2$COOH, N$_3$, CH$_2$N$_3$, alkyl, alkenyl, or alkynyl;
R$^4$ and R$^5$ are independently selected from the group comprising H, OH, OCH$_3$, OC$_2$H$_5$, —COOH, CH$_2$COOH, N$_3$, CH$_2$N$_3$, alkyl, alkenyl, or alkynyl;

-continued

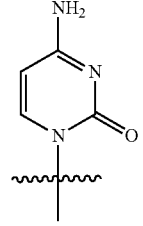

formula 6 formula 7

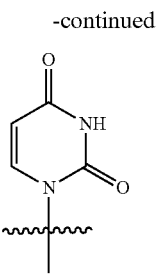

In the method of synthesis with the imidazolide derivative, preferably the reaction is
carried out in the presence of divalent metal chloride, wherein the preferred divalent metal chloride is zinc chloride $ZnCl_2$.

In the method of synthesis with the imidazolide derivative, preferably a 1.5-fold excess of imidazolide according to formula 9 over phosphate group, thiophosphate group, or the compound according to formula 2a is utilized, in the presence of 8-fold excess of divalent metal chloride.

The present invention also relates to a pharmaceutical formulation comprising the 5'-phosphorothiolate cap analog according to the invention and a pharmaceutically acceptable carrier.

The pharmaceutical formulation according to the invention comprising the 5'-phosphorothiolate cap analog according to the invention and a pharmaceutically acceptable carrier has properties of inhibiting DcpS activity, preferably inhibiting hDcpS activity, and is intended for use in SMA treatment.

The selection of a pharmaceutically acceptable carrier will be dependent on the method of administering the pharmaceutical formulation and on the necessity of protecting the 5'-phosphorothiolate analog according to the invention from inactivation of degradation, before delivering into cells, tissues, or an organism. The pharmaceutically acceptable carriers include solvents, dispersing media and auxiliary agents (coating materials, surfactants, aromas and flavors, antioxidants and others). The pharmaceutical formulation according to the invention can be administered by different routes, including injection, oral, topical and rectal administration. A dose of a pharmaceutical formulation is established accounting for the route of administration, the condition requiring treatment or prophylactics, and other relevant circumstances.

The invention also relates to an mRNA comprising at the 5' end the novel 5'-phosphorothiolate cap analog according to the invention.
The preferred mRNA is characterized by the 5'-phosphorothiolate cap analog being selected from a group comprising $m^7GSpppG$ (no. 24), $m^{7,2'O}GSpppG$ (no. 26), $m^7GSpppSG$ (no. 32), $m^7GSpp_spG$ D1 (no. 30), $m^7GSpp_spG$ D2 (no. 31), $m^7GSpp_spSG$ D1 (no. 33), $m^7GSpp_spSG$ D2 (no. 34), more preferably it is $m^{7,2'O}GSpppG$ (no. 26).
The present invention also relates to a method of preparation of mRNA comprising a 5'-phosphorothiolate cap analog at the 5'-end of the molecule, said method comprising: incorporation of the 5'-phosphorothiolate cap analog according to the invention into the mRNA molecule during synthesis.

In a preferred method of preparation of mRNA the 5'-phosphorothiolate cap analog is selected from a group comprising $m^7GSpppG$ (no. 24), $m^{7,2'O}GSpppG$ (no. 26), $m^7GSpppSG$ (no. 32), $m^7GSpp_spG$ D1 (no. 30), $m^7GSpp_spG$ D2 (no. 31), $m^7GSpp_spSG$ D1 (no. 33), $m^7GSpp_spSG$ D2 (no. 34), more preferably it is $m^{7,2'O}GSpppG$ (no. 26).

In a preferred method of preparation of mRNA, the synthesis of mRNA proceeds through transcription in vitro.

The invention also relates to mRNA prepared by the method of preparation of mRNA comprising the 5'-phosphorothiolate cap analog according to the invention at the 5'-end of the molecule.

The invention also relates to a use of the mRNA comprising the 5'-phosphorothiolate cap analog according to the invention at the 5'-end of the molecule for production of proteins.

The use of mRNA for production of proteins is preferably carried out in a cellular or a non-cellular system.

The invention also relates to the mRNA according to the invention and the one prepared according to the method of preparation of mRNA comprising the 5'-phosphorothiolate cap analog according to the invention at the 5' end of the molecule for use as a medicament.

Such mRNA is preferably used as a medicament for treatment of spinal muscular atrophy (SMA) an/or for alleviation of symptoms of SMA.

Preferably, such mRNA is utilized for use as an anti-cancer medicament, more preferably as a medicament in anti-cancer immunotherapy.

The invention also relates to a use of the mRNA according to the invention and the one prepared according to the method of preparation of mRNA comprising the 5'-phosphorothiolate analog according to the invention at the 5' end of the molecule in production of a medicament.

In a preferred use, mRNA is used for preparation of a medicament for treatment of spinal muscular atrophy (SMA) an/or for alleviation of symptoms of SMA, as an anti-cancer medicament, more preferably as a medicament in anti-cancer immunotherapy.

The invention also relates to a pharmaceutical formulation, comprising the mRNA according to the invention and the one prepared by the method of preparation of mRNA comprising the 5'-phosphorothiolate analog according to the invention at the 5' end of the molecule and a pharmaceutically acceptable carrier.

Unmethylated compounds (GppSG and GpppSG) were synthesized as controls for biological studies.

Table 1 lists alkylating agents used for the synthesis of appropriately modified nucleotides which were obtained for the first time by the inventors. Tables 2 and 3 list 5'-phosphorothiolate cap analogs obtained and subsequently characterized by biophysical and biochemical methods.

Among the compounds listed in Table 2 and Table 3, particularly preferred in relation to SMA treatment are the 5'-phosphorothiolate analogs comprising sulfur at the 5'-position from the side of 7-methylguanosine (compounds no. 12, 23, 24, 25, 26, 30, 31, 32, 33, 34 and 37), which are characterized by stability in the presence of DcpS enzyme.

TABLE 1

5'-deoxy-5'-iodo-guanosine analogs (compound numbers indicated next to the structures)

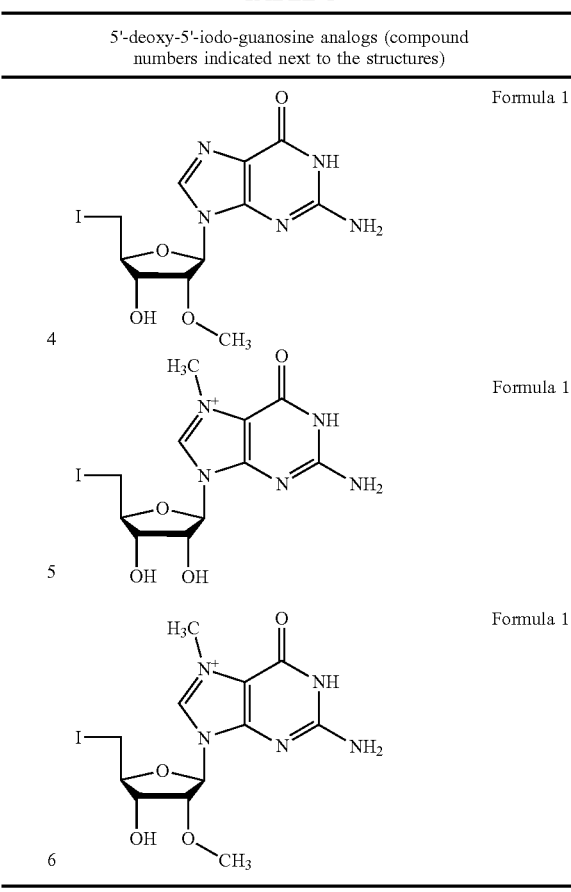

TABLE 2

Mononucleotide 5'-thiophosphate analogs: panel A - guanosine, panel B - 7-methyloguanosine

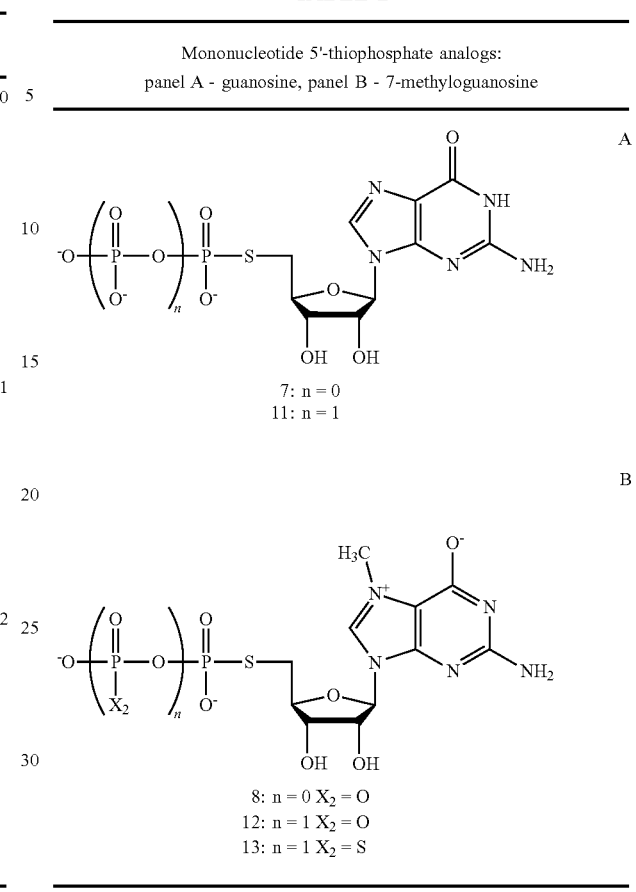

A

7: n = 0
11: n = 1

B

8: n = 0 X$_2$ = O
12: n = 1 X$_2$ = O
13: n = 1 X$_2$ = S

Formula 10

Formula 11

Formula 12

TABLE 3

5'-Thiophosphate cap analogs

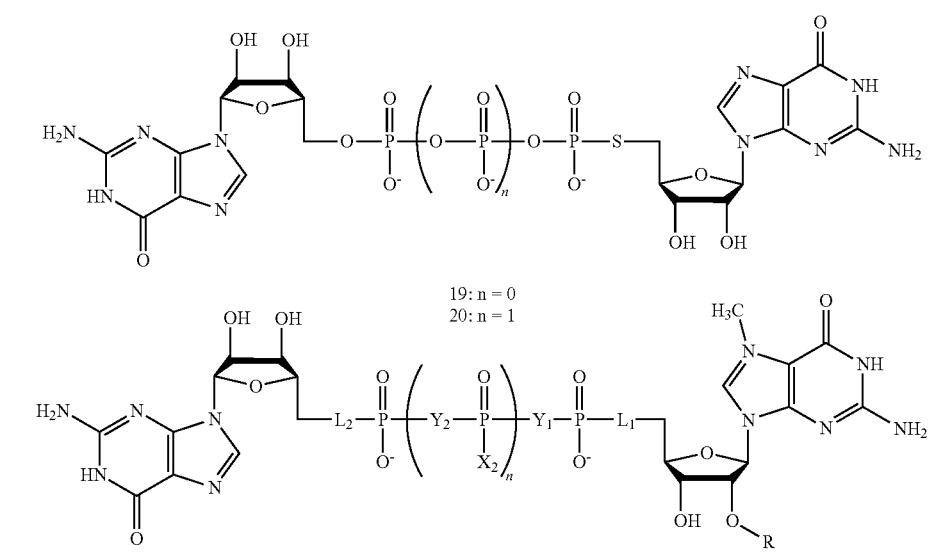

19: n = 0
20: n = 1

| Compound number | Compound | n | R | L$_1$ | L$_2$ | Y$_1$ | Y$_2$ | X$_2$ |
|---|---|---|---|---|---|---|---|---|
| 21 | m$^7$GppSG | 0 | H | O | S | O | O | O |
| 22 | m$^7$GpppSG | 1 | H | O | S | O | O | O |
| 23 | m$^7$GSppG | 0 | H | S | O | O | O | O |

TABLE 3-continued

| | | | | | | | | |
|---|---|---|---|---|---|---|---|---|
| 24 | $m^7GSpppG$ | 1 | H | S | O | O | O | O |
| 25 | $m^7GSppCH_2pG$ | 1 | H | S | O | O | $CH_2$ | O |
| 38 | $m^{7,2'O}GpppSG$ | 1 | $CH_3$ | O | S | O | O | O |
| 26 | $m^{7,2'O}GSpppG$ | 1 | $CH_3$ | S | O | O | O | O |
| 32 | $m^7GSpppSG$ | 1 | H | S | S | O | O | O |
| 35 | $m^7Gpp_spSG$ D1 | 1 | H | O | S | O | O | S |
| 36 | $m^7Gpp_spSG$ D2 | 1 | H | O | S | O | O | S |
| 30 | $m^7GSpp_spG$ D1 | 1 | H | S | O | O | O | S |
| 31 | $m^7GSpp_spG$ D2 | 1 | H | S | O | O | O | S |
| 33 | $m^7GSpp_spSG$ D1 | 1 | H | S | S | O | O | S |
| 34 | $m^7GSpp_spSG$ D2 | 1 | H | S | S | O | O | S |
| 37 | $m^7GpCH_2ppSG$ | 1 | H | O | S | $CH_2$ | O | O |

The documents cited in the description and documents referenced therein are also hereby incorporated by reference.

BRIEF DESCRIPTION OF DRAWINGS

For better understanding of the invention it was illustrated with examples and on the attached figures wherein:

FIG. 8. Illustrates susceptibility to Dcp1/2 enzyme activity of short 26 nt RNAs capped with various cap analogs (transcripts without cap at their 5' ends are 25 nt long) being incubated with the SpDcp1/2 decapping enzyme. The reactions were conducted for 0, 5, 15, 30 min, after termination thereof reaction mixture was resolved on denaturing 15% polyacrylamide gel, after the electrophoretic separation was completed the gel was stained with SYBR-Gold (Invitrogen). On each panel the leftmost lane refers to the control, which is uncapped RNA.

FIG. 9. Illustrates relative susceptibility to Dcp1/2 enzyme activity determined from the data on FIG. 8. The relative susceptibility to Dcp1/2 activity was calculated as the ratio of intensity of the band corresponding to the RNA capped at the 5' end to the sum of the intensities of bands corresponding to capped and uncapped RNA. All values were normalized in relation to time 0 min for individual RNAs.

FIG. 10. Illustrates relative translational efficiency obtained from measurements of translation efficiencies of mRNA encoding *Renilla* luciferase capped with various cap analogs on the 5' end in rabbit reticulocyte extract.

FIG. 11. Illustrates relative translational efficiency in HeLa cells determined on the basis of luciferase activity at selected time points. Results are presented as a ratio of luciferase activity measured for lysate of cells transfected with mRNA capped with $m_2^{7,2'\text{-}O}GSpppG$ or $m_2^{7,2'\text{-}O}GpppSG$ on the 5' end to luciferase activity measured for lysate of cells transfected with mRNA capped with $m^7GpppG$. The histograms represent the mean value from three biological repetitions.

Chemical synthesis of 5'-thiophosphate cap analogs is a creative combination of three nucleotide synthesis methods based on chemistry of:

1) Imidazolide nucleotide derivatives (see (Abrams and Schiff 1973); (Barnes, Waldrop et al. 1983); (Kalek, Jemielity et al. 2006) and (Kalek, Jemielity et al. 2005))
2) S-alkylation by halogen containing nucleoside derivatives (see (Arakawa, Shiokawa et al. 2003))
3) Synthesis of terminal nucleoside β-thio-di and γ-thiotriphosphates (see (Zuberek, Jemielity et al. 2003))

Figure 2:
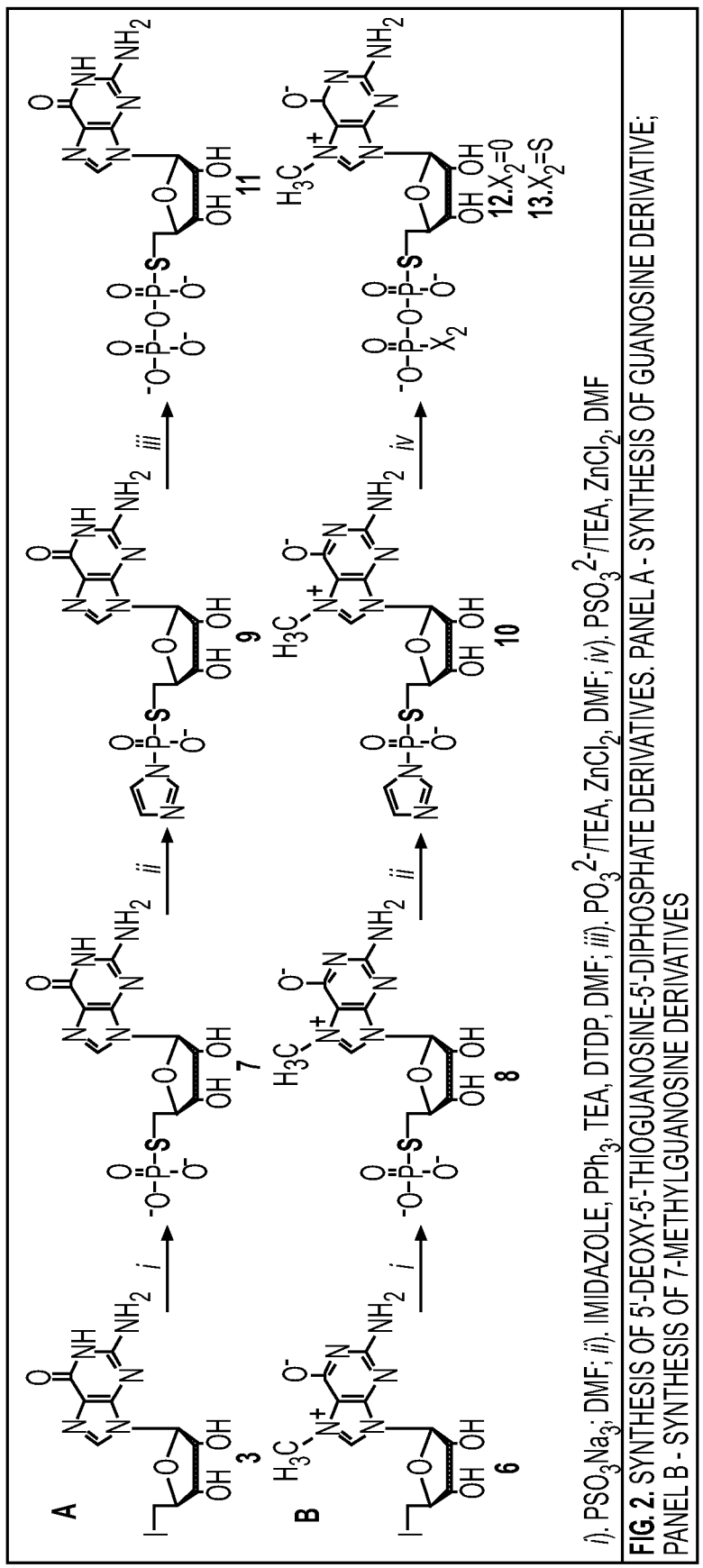
FIG. 2 Illustrates synthesis of 5'-deoxy-5'-thioguanosine-5'-thiophosphates. A—synthesis of guanosine derivative; B—synthesis of 7-methyloguanosine derivatives.
Figure 3:
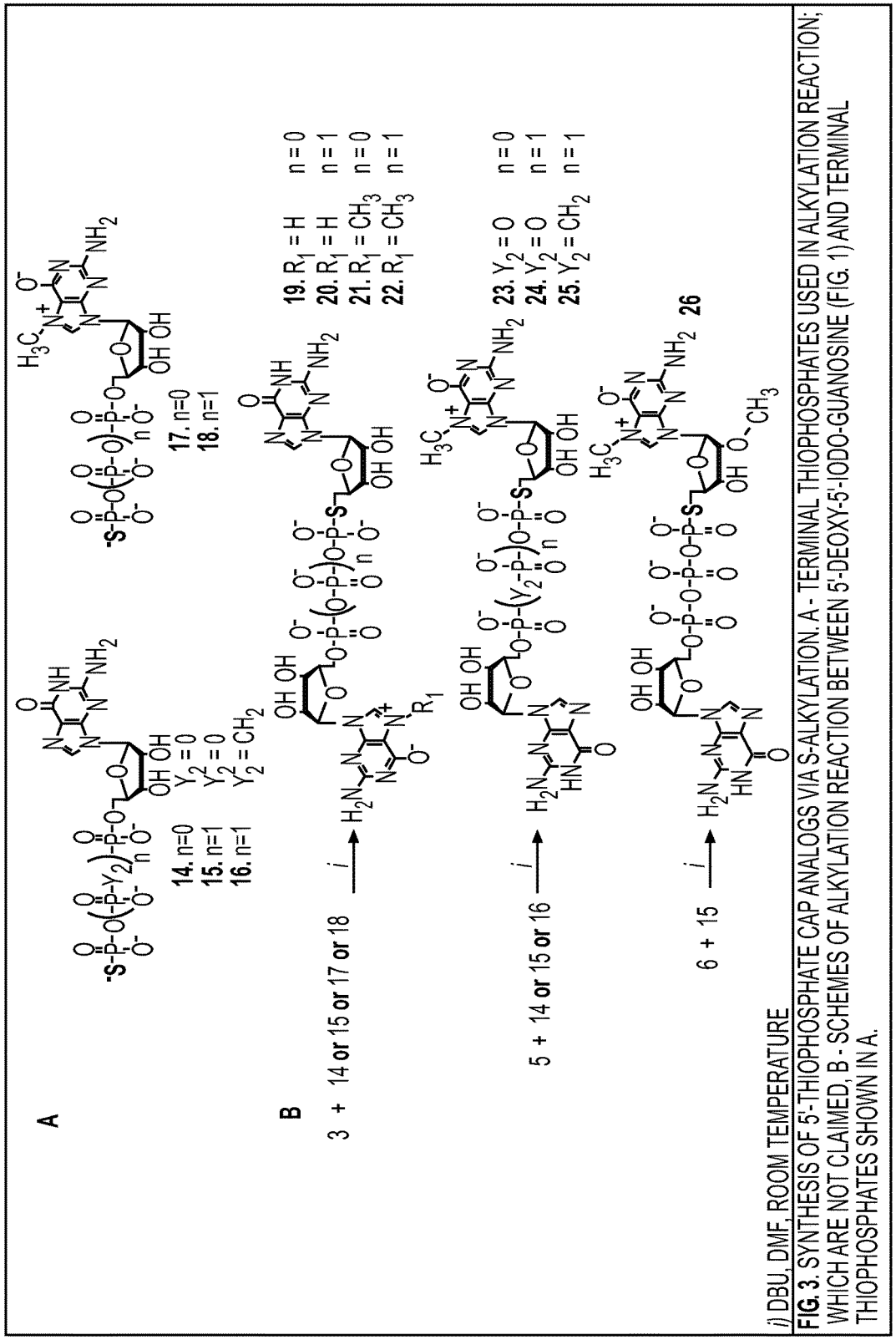
FIG. 3 Illustrates synthesis of 5'-thiophosphate cap analogs via S-alkylation. A—terminal thiophosphates used in alkylation reaction; B—schemes of alkylation reaction using 5'-deoxy-5'-iodo-guanosine (z FIG. 1) and terminal thiophosphates shown in A.
Figure 4:
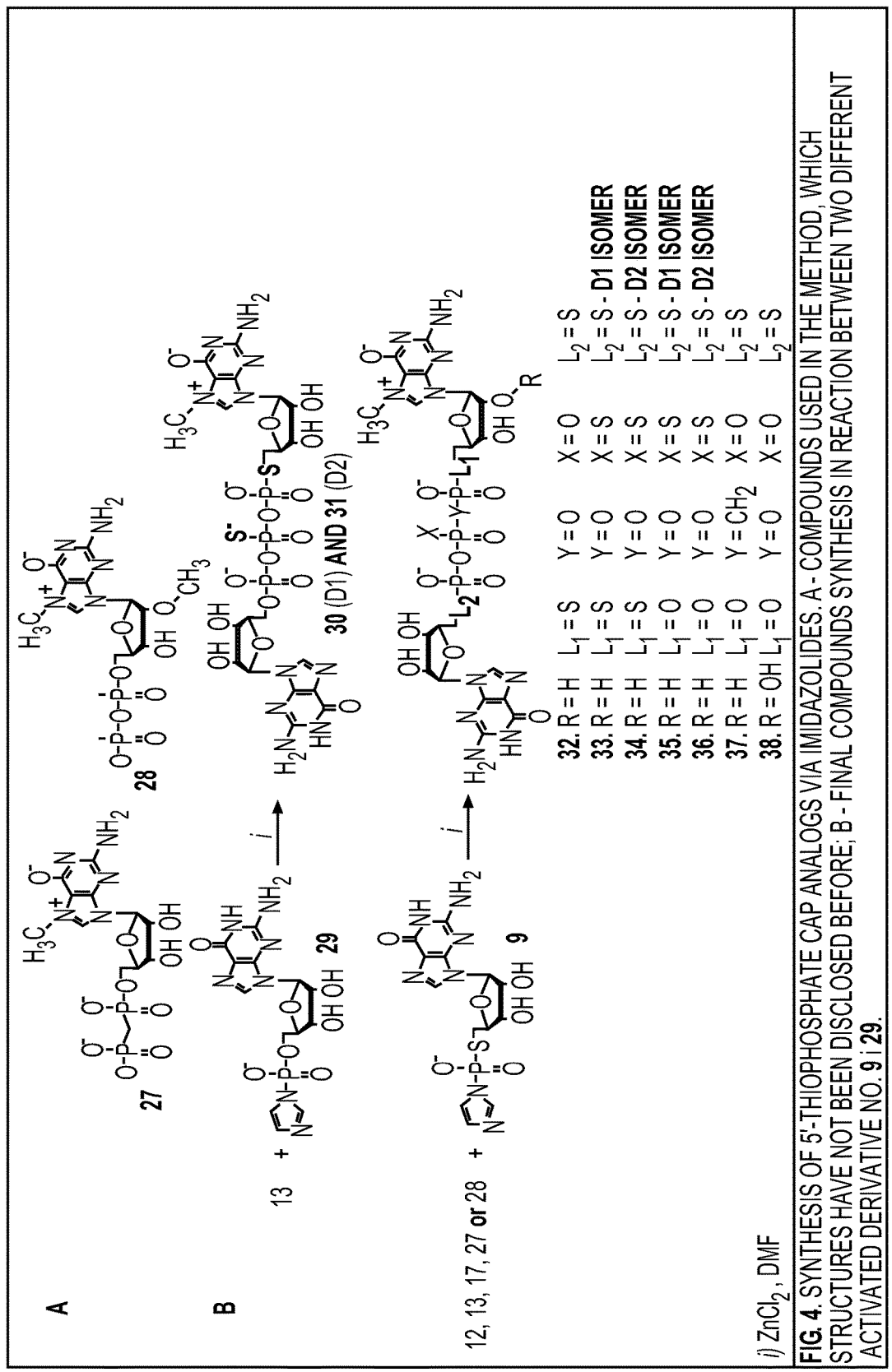
FIG. 4 Illustrates synthesis of 5'-thiophosphate cap analogs via imidazolides. A—compounds used in the method; B—final compounds synthesis using two different activated derivatives no. 9 i 29.

In order to synthesize sulfur-containing cap analogs at the 5'-position we developed two complementary approaches that on the whole allow synthesis of a whole variety of 5'-phosphorothioate analogs of mono-, di-, and triphosphates of nucleosides and dinucleotide cap analogs (FIG. 2-4). Approach 1 (FIG. 2 and the first step in FIG. 3) involves the reaction of S-alkylation using a nucleophilic substitution reaction of 5'-deoxy-5'-iodonucleoside by β- or γ-thiophosphates. The second approach (FIG. 4) yielding dinucleotide compounds having sulfur atom at the 5' position, uses a coupling reaction between the prior activated form of an appropriate imidazolide nucleotide and diphosphate (in both cases, at a chosen stage the reaction of S-alkylation was used) in the presence of $ZnCl_2$ as a catalyst.

The first approach uses the corresponding phosphorothioates (mono-, di-, tri-) bearing at a terminal position a phosphorothioate moiety. The optimum conditions for this reaction is the use of equimolar amounts of phosphorothioate, 5'-iodonucleoside and DBU (1,8-diazabicyclo (5.4.0) undec-7-ene) as a base. To date, using this method, we obtained 9 different dinucleotide cap analogs including two units containing methylene modifications at positions α-β and β-γ of triphosphate bridge (FIG. 3).

The second method for the efficient yield required the presence of divalent metal chlorides such as $ZnCl_2$, which also improves the solubility in an organic medium, protects against hydrolysis of imidazolide derivative and accelerates the reaction rate by getting the imidazole derivative and the phosphate of the other molecule closer to one another. The optimum conditions for this reaction was the use of 1.5 equivalents of the imidazole derivative relative to the diphosphate in the presence of 8-fold excess of $ZnCl_2$ in DMF. Using the second method we obtained further nine 5'-phosphorothioate cap analogs containing two sulfurs at the 5'position and sulfur at the β-nonbridging position in the triphosphate chain (FIG. 4). To date the use of 5'-phosphorothioate analogs of nucleotides in this type of reaction have not been described. Due to the presence of a stereogenic center located on the phosphorus atom, each analog containing β-S-sulfur atom was obtained as a mixture of diastereomers (called D1 and D2 according to the order of their elution from the RP-HPLC column). The individual diastereomers were separated by RP-HPLC.

The obtained cap analogs were purified by ion exchange chromatography, DEAE Sephadex A-25, and if the purity was not sufficient, by preparative HPLC. Then, the purified compounds were tested for their biochemical and biological properties.

The synthesis routes leading to cap analogs containing sulfur atom at the 5' position are shown in FIGS. 1-4.

Figure 5:
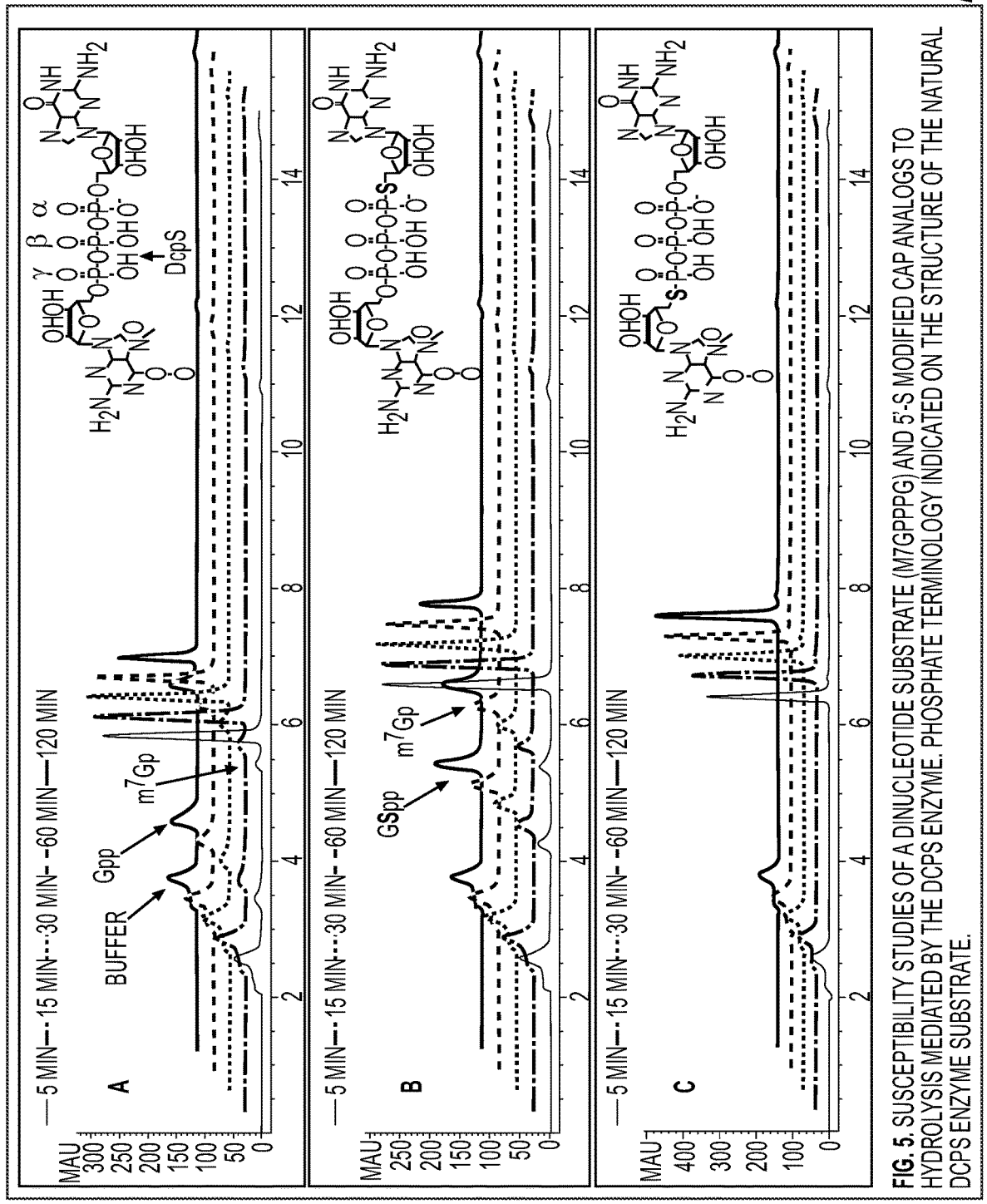
FIG. 5 Illustrates hydrolysis of natural dinucleotide substrate by DcpS and stability studies of 5'-S modified analogs: panel A—stability studies of natural cap analog $m^7GpppG$ against DcpS; panel B—stability studies of cap analog no. 20 against DcpS enzyme (Table 3); panel C—stability studies of cap analog no. 21 against DcpS enzyme (Table 3).
Figure 6:
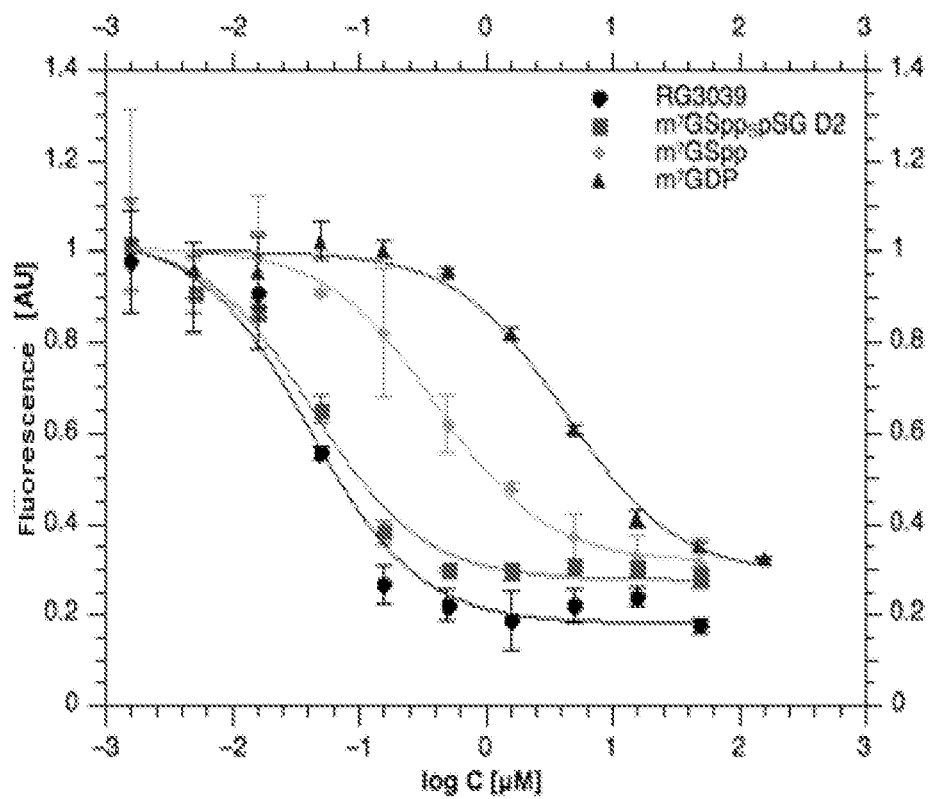
FIG. 6. The result of $IC_{50}$ determination for compounds: $m^7GSpp_spSG$ D2, $m^7GSpp$, $m^7GDP$ and RG3039.

The obtained cap analogs were then tested as substrates of the human enzyme DcpS (hDcpS). As determined by using reverse phase HPLC (RP HPLC), only four of the analogs: $m^7$GppSG (no. 21), $m^7$GpppSG (no. 22) $m^{7,2'-O}$GpppSG (no. 38) and $m^7$Gpp$_s$pSG D1/D2 (no. 35-36) are hydrolyzed by DcpS. Other analogs containing sulfur atom at the 5' position from the side of the 7-methylated guanosine are resistant to hydrolysis by hDcpS (stability comparison of two different analogs (no. 22) and (no. 24)—FIG. 5, Table 4). In contrast to the compounds no. 21, 22, 38 and 35-36, analog 37 ($m^7$GpCH$_2$ppSG) was additionally modified with a methylenebisphosphonate moiety, and was also resistant to hydrolysis by the enzyme hDcpS (Table 5). Then, the fluorescence method and fluorogenic probe were used for determining the ability of these compounds to inhibit the enzyme hDcpS while determining for the compounds which are resistant to the enzyme activity the parameter IC$_{50}$ (see patent application PL406893). After the studies, it was discovered that the resulting compounds are very good inhibitors of the human enzyme DcpS.

Figure 7:
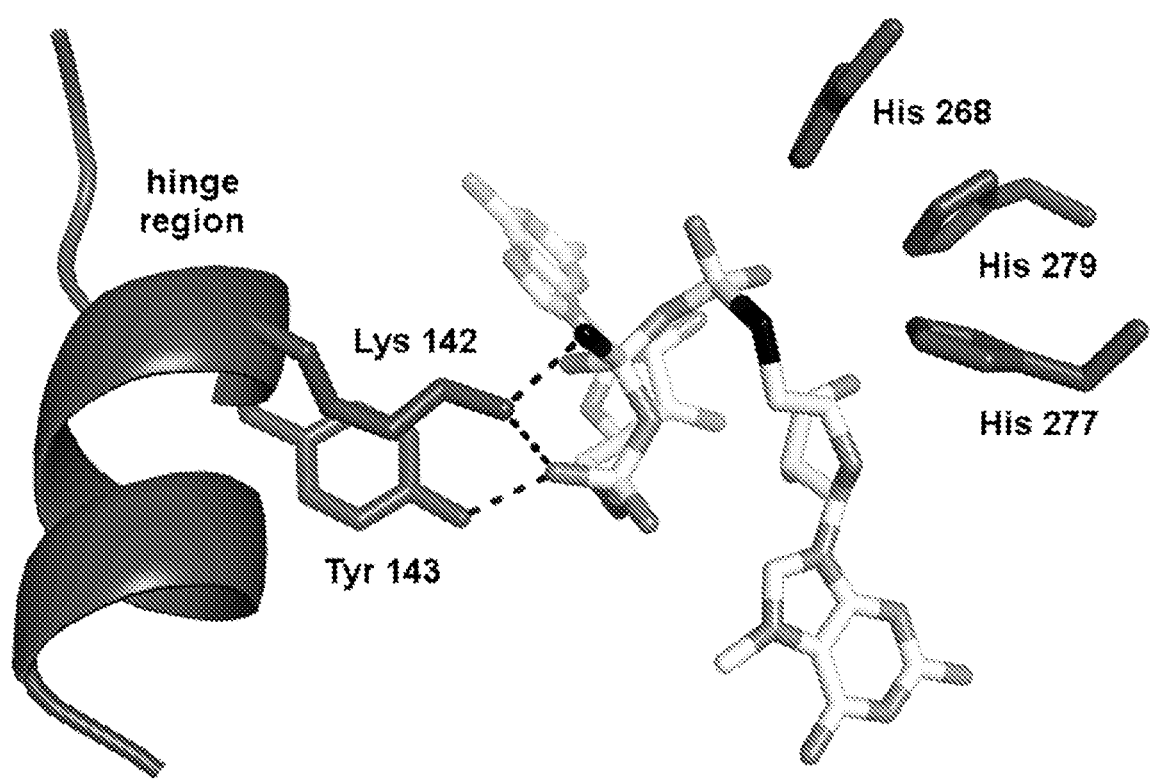
FIG. 7. Illustrates a crystal structure of active site of the enzyme ΔN37hDcpS in complex with $m^7GSpp_spSG$ D2.

Analog no. 34, displaying the best inhibitory properties against hDcpS enzyme from all tested cap analogs, was co-crystallized with a shortened version of the enzyme (ΔN37hDcpS; full-length enzyme did not form crystals), and the 2.05 Å resolution structure of the complex was determined by X-Ray crystallography (FIG. 7). Conformation of the analog No. 34 observed in the complex structure differs significantly from the conformation of a non-modified cap analog $m^7$GpppG (compound No. 0) in complex with a catalytically-inactive H277N hDcpS mutant (Gu, Fabrega et al. 2004). Particularly substantial differences between those two ligands were observed in the alignment of the triphosphate bridge, resulting in exclusion of γ phosphate of the analog no. 34 from the catalytic center Additionally, besides the typical cap/DcpS enzyme complex interactions with the C-terminal domain, analog no. 34 interacts through hydrogen bonds with the lysine 142 and tyrosine 143 residues. Those amino acids are located in the so-called hinge region, connecting C- and N-terminal domains, which move relative to each other during the catalytic cycle.

The structure and purity of the obtained compounds were confirmed by mass spectrometry and $^1$H and $^{31}$P NMR.

The observation that $m^7$GSpppG (Compound no. 24) and its analogs are resistant to hDcpS is unexpected because the hydrolysis of obtained compounds proceeds through a nucleophilic attack on the phosphate group adjacent to 7-methylguanosine, which is consistent with the catalytic mechanism established for the natural substrates.

In summary, the invention describes structures and methods for synthesis of various analogs of the 5' end of the mRNA (cap) containing 5'-phosphorothioate moiety. None of the cap analogs described, their properties against the enzyme DcpS, nor methods of their use, particularly for the treatment of spinal muscular atrophy (SMA) and/or alleviating the symptoms of SMA have been previously described in the literature.

Selected analogs were used for mRNA synthesis using in vitro transcription method with RNA SP6 polymerase (New England BioLabs). It was examined which percentage of the pool of transcripts with a length of 35 nucleotides has a cap structure, and then the susceptibility of these transcripts to degradation by a recombinant enzyme Dcp1/2 from *Schizosaccharomyces pombe* was examined (Example 2, Test 4, FIG. 8, FIG. 9, Tab. 6.). Full-length transcripts encoding luciferase (as a reporter gene) were subjected to translation in rabbit reticulocyte lysate (FIG. 10, Example 2, Test 5) and in HeLa cells transfected with modified mRNA (FIG. 11, Example 2, Test 6). In both cases, the efficiency of mRNA translation in both translational systems was determined by examining the activity of the synthesized protein (luciferase) (Tab. 6).

The terms used in the description have the following meanings. Terms not defined herein have the meaning that is presented and understood by a person skilled in the art in light of this disclosure and the context of the description of the patent application. The following conventions, unless stated otherwise, were used in the present description, the terms having the meanings indicated as in the definitions below.

The term "alkyl" refers to a saturated, linear or branched hydrocarbonyl substituent having the indicated number of carbon atoms. The examples of an alkyl substituent are -methyl, -ethyl, -n-propyl, -n-butyl, -n-pentyl, -n-hexyl, -n-heptyl, -n-octyl, -n-nonyl and -n-decyl. Representative branched —(C1-C10)alkyls include -isopropyl, -sec-butyl, -isobutyl, -tert-butyl, -isopentyl, -neopentyl, -1-methylbutyl, -2-methylbutyl, -3-methylbutyl, -1,1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylbutyl, 1,3-dimethylbutyl, -2,2-dimethylbutyl, -2,3-dimethylbutyl, -3,3-dimethyl-butyl, -1-methylhexyl, 2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, 1,2-di-methylheptyl, -1,3-dimethylheptyl and -3,3-dimethylheptyl and others. The term "alkenyl" refers to a saturated, linear or branched acyclic hydrocarbyl substituent having the indicated number of carbon atoms and containing at least one carbon-carbon double bonds. The examples of an alkenyl substituent are -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and others.

The term "alkynyl" refers to a saturated, linear or branched acyclic hydrocarbyl substituent having the indicated number of carbon atoms and containing at least one carbon-carbon triple bond. The examples of an alkynyl substituent are acetylenyl, propynyl, -1-butynyl, -2-butynyl, -1-pentynyl, -2-pentynyl, -3-methyl-1-butynyl, 4-pentynyl, -1-hexynyl, -2-hexynyl, -5-hexynyl and others.

The term "heteroatom" refers to an atom selected from the group of oxygen, sulfur, nitrogen, phosphorus and others.

The term "HPLC" refers to high performance liquid chromatography, and the solvents designated as solvents for "HPLC" mean solvents of suitable purity for HPLC analysis (High Performance Liquid Chromatography).

The term "NMR" means nuclear magnetic resonance.

The term "cellular system" refers to cells capable of carrying out a protein biosynthesis process on an RNA template.

The term "non-cellular system" means a biological mixture containing all the ingredients necessary for protein biosynthesis on the basis of an RNA template, usually a lysate of animal or plant cells.

MODES FOR CARRYING OUT THE INVENTION

The following examples are provided merely to illustrate the invention and to explain its various aspects, and not for its limitation, and should not be equated with its all scope, which is defined in the appended claims. The following examples, unless stated otherwise, involved the use of standard materials and methods used in the field or the procedures recommended by the manufacturer for the particular materials and methods.

EXAMPLES

General Information Related to the Synthesis, Isolation and Characterization of New Cap Analogs Nucleotides which were intermediates were purified by ionexchange chromatography on DEAE Sephadex A-25 ($HCO_3^-$ form) using a linear gradient of triethylammonium bicarbonate (TEAB) in deionized water. After evaporation under reduced pressure, during which 96% ethanol was added several times to decompose the TEAB buffer, intermediates were isolated as a triethyalammonium salts. The final products (cap analogs) were purified in the same manner and then purified by semi-preparative HPLC, and subjected to lyophilization several times and were isolated as ammonium salts. Analytical reverse phase HPLC (RP HPLC) was performed on Agilent Technologies Series 1200 apparatus, with Supelcosil LC-18 RP-T column (4.6×250 mm, flow 1.3 ml/min) with a linear gradient of 0%-25% methanol (program A) in 0.05 M ammonium acetate (pH 5.9) or 0%-50% methanol (program B) in 0.05 M ammonium acetate (pH 5.9). The eluted compounds were detected using UV-VIS detector (at 260 nm) and fluorescence detector (excitation 260 nm, emission 370 nm). Preparative RP HPLC was carried out on the same apparatus using a Discovery RP Amide C16 column (21.2 mm×250 mm, flow 5.0 ml/min) using a linear gradient of acetonitrile in 0.05 M ammonium acetate (pH 5.9) as the mobile phase. $^1$H NMR and $^{31}$P NMR spectra were recorded at 25° C. on a Varian UNITY-plus at a frequency of 399.94 MHz and 161.90 MHz respectively. $^1$H NMR chemical shifts were reported to TSP (3-trimethylsilyl [2,2,3,3-D4] sodium propionate) in $D_2O$ (internal standard). $^{31}$P NMR chemical shifts were reported to 20% phosphoric acid in D20 (external standard). The high resolution mass spectra in negative [MS ESI (−)] or positive ion mode [MS ESI (+)] were recorded on a Micromass QToF 1 MS. Reading the fluorescence plate reader was performed on a Tecan Infinit 200 ® PRO with excitation at 480 nm and emission at 535 nm. Samples were placed in a black 96-well plate (Greiner). Crystallisations were performed on 96-well plates with 3-lens wells (Swissci), utilizing a pipetting robot Mosquito Crystal (TTp Labtech). Solvents and other reagents were purchased from Sigma-Aldrich and used without further purification, unless stated otherwise below. Commercially available sodium salts of GMP and GDP were converted to triethylammonium salts using ion exchange chromatography on Dowex 50 WX8. Triethylammonium salts and $m^7$GMP and $m^7$GDP sodium salts, $m^7$GMP-Im and $m^7$GDP-Im were obtained as described in the literature (Kalek, Jemielity et al. 2005), (Jemielity, Fowler et al. 2003). 5'-deoxy-5'-iodo-guanosine, 5'-deoxy-5'-thiogaunosin-5'-monothiophosphate and triethylamine phosphorothioate were obtained as described in the literature ((Arakawa, Shiokawa et al. 2003), (Zuberek, Jemielity et al. 2003)). $m^7$GpCH2p triethylammonium salt was prepared as described in the literature (Kalek, Jemielity et al. 2006). GpCH$_2$ppS was prepared as described (Kowalska, Ziemniak et al. 2008)

In the examples below, in the brackets for specific compounds the reference to the figure and the number indicating the specified substituents is given, which corresponds to a particular number for the particular cap analog.

Example 1. Synthesis and Isolation of New Cap Analogs

Figure 1:
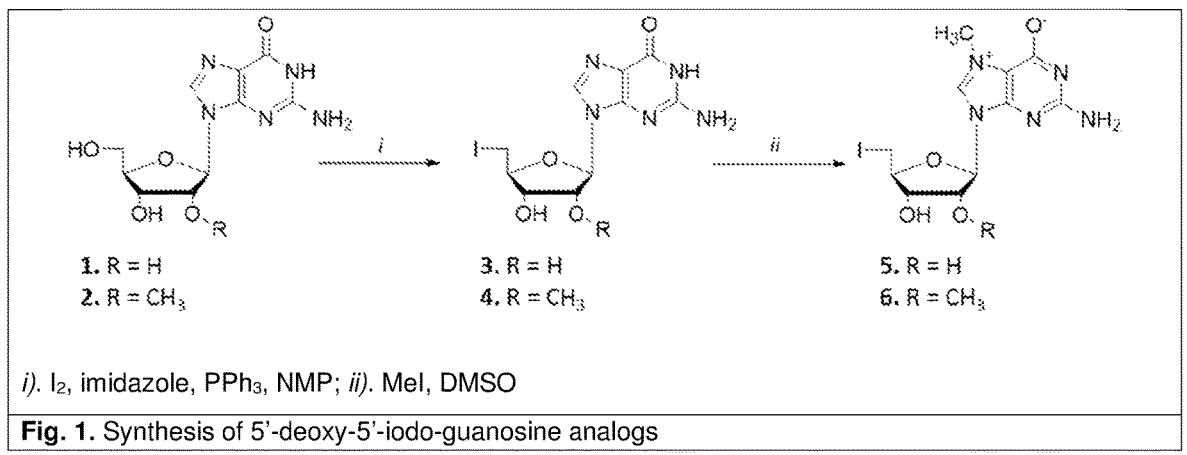
FIG. 1 Illustrates synthesis of 5'-deoxy-5'-iodo-guanosine analogs

General Method of Synthesis of 5'-Iodo Nucloside Derivatives (FIG. 1, No. 3, 4)

Iodine (3 mmol, M=253.81 g/mol was added over 5 min to a magnetically stirred suspension of the corresponding nucleoside (1 mmol), triphenylphosphine (3 mmol, M=262.29 g/mol) and imidazole (6 mmol, M=68.08 g/mol) in N-methyl-2-pyrrolidinone (to a concentration of nucleoside 0.25 mol/l) at room temperature. The reaction was performed over 3 h, and the progress of the reaction was monitored using RP HPLC. Then, the reaction mixture was poured into a solution of $CH_2Cl_2:H_2O$ (3:1, v/v), diluting the reaction mixture 12-times. A white crystalline precipitate formed during 24 h in 4° C., at the interface of the two layers. The precipitate was filtered off under reduced pressure, washed with methylene chloride and dried in vacuum over $P_2O_5$.

5'-deoxy-5'-iodo-guanosine (FIG. 1, No. 3)

5'-deoxy-5'-iodo-guanosine (FIG. 1, no. 3), (10.4 g, 26.5 mmol, 75%) was obtained starting from guanosine (FIG. 1, no. 1), (10 g, 35.3 mmol) following the general procedure. $t_R$ (B)=12.36 min;

$^1$H NMR (400 MHz, DMSO-$d_6$) δ ppm 10.65 (s, 1H, H-1), 7.89 (s, 1H, H-8), 6.47 (bs, 2H, NH2), 5.68 (d, 1H, J=6.26 Hz, H-1'), 5.51 (d, 1H, J=6.26 Hz, 2'-OH), 5.35 (d, 1H, J=4.70 Hz, 3'-OH), 4.59 (q, 1H, J=5.48 Hz, H-2'), 4.03 (q, 1H, J=5.09, 3.13 Hz, H-3'), 3.90 (dt, 1H, J=6.26, 3.13 Hz, H-4'), 3.53 (dd, 1H, J=6.26, 5.87 Hz, H-5'), 3.39 (dd, 1H, J=10.17, 6.65 Hz, H-5'); HRMS ESI (−) calcd. m/z for $C_{10}H_{11}IN_5O_4^-$, (M−H)$^-$; 391.9861, found 391.98610.

5'-deoxy-5'-iodo-2'-O-methyl-guanosine (FIG. 1, No. 4)

2'-O-methyl-5'-deoxy-5'-iodo-guanosine (FIG. 1, no. 4), (328.8 mg, 0.81 mmol, 80%) was obtained starting from 2'-O-methylguanosine (FIG. 1, no. 2) (300 mg, 1.0 mmol) following the general procedure. $t_R$ (B)=14.44 min;

$^1$H NMR (400 MHz, DMSO-$d_6$) δ ppm 7.95 (s, 1H, H-8), 6.50 (bs, 2H, NH2), 5.81 (d, 1H, J=6.41 Hz, H-1'), 5.50 (d, 1H, J=5.34 Hz, 3'-OH), 4.41, 4.40 (2d, 1H, J=6.26, 6.41 Hz, H-2'), 4.28-4.25 (m, 1H, H-3'), 3.97, 3.96 (2t, 1H, J=6.56, 3.05 Hz, H-4'), 3.56 (dd, 1H, J=6.41, 10.38 Hz, H-5'), 3.43 (dd, 1H, J=10.53, 6.87, 6.71 Hz, H-5'), 3.30 (s, 3H, $CH_3$);

HRMS ESI (−) calcd. m/z for $C_{11}H_{13}IN_5O_4^-$ [M−H]⁻: 406.0090, found 406.0021.

5'-deoxy-5'-iodo-7-methylguanosine (FIG. 1, No. 5)

5'-deoxy-5'-iodo-guanosine (FIG. 1, no. 3) (2 g, 5.09 mmol) was dissolved in anhydrous DMF (20 mL) and MeI (2.5 mL, 40.7 mmol) was added. Reaction mixture was stirred on magnetic stirrer at room temperature. The reaction progress was monitored by RP HPLC. When no starting material was observed, reaction was stopped by adding water (10 mL), and the excess of methyl iodide was evaporated under vacuum and reaction mixture was concentrated under reduced pressure. Then, to the remaining crude product $CH_2Cl_2$ (100 mL) was added and yellow precipitate was formed. Precipitate was filtered off, under reduced pressure, washed with $CH_2Cl_2$ (3×20 mL) and dried for 24 h in vacuum over $P_4O_{10}$. Yield 1.6 g (77.0%). $t_R$ (B)=11.94 min;
¹H NMR (400 MHz, $D_2O$) δ ppm 5.98 (d, 1H, J=3.91 Hz, H-1'), 4.81 (dd, 1H, J=4.70 Hz, H-2'), 4.31 (t, 1H, J=5.09, H-3'), 4.15 (q, 1H, J=5.48, H-4'), 4.07 (s, 3H, $CH_3$), 3.50-3.62 (m, 2H, J=4.70, 5.87 Hz, H-5');
HRMS ESI (+) calcd. m/z $C_{11}H_{15}IN_5O_4^+$[M+H]⁺: 408.01687, found 408.01163.

5'-deoxy-5'-iodo-2'-O-methyl-7-methylguanosine (FIG. 1, No. 6)

5'-deoxy-5'-iodo-2'-O-methylguanosine (FIG. 1, no. 4) (200.8 mg, 0.49 mmol) was dissolved in anhydrous DMSO (3.3 mL) and MeI (0.25 mL, 3.9 mmol) was added. Reaction mixture was stirred on magnetic stirrer at room temperature. The reaction progress was monitored by RP HPLC. When no starting material was observed, reaction was quenched with water (10 mL) and pH was adjusted to neutral using $NaHCO_3$, excess of methyl iodode was extracted with diethyl ether and the water phases were polled, followed by concentrating the mixture and purification by preparative HPLC obtaining 45.8 mg of the compound (77%). $t_R$ (B)=11.94 min;
¹H NMR (400 MHz, DMSO-$d_6$) b ppm 9.03 (s, 1H, H-8), 6.39 (bs, 2H, NH2), 5.95 (d, 1H, J=4.27 Hz, H-1'), 4.40 (t, 1H, J=4.58 Hz, H-2'), 4.24 (t, 1H, J=4.88 Hz, H-3'), 4.08-4.06 (m, 1H, H-4'), 4.02 (s, 3H, $CH_3$), 3.59 (dd, 1H, J=5.19, 4.88, 10.68 Hz, H-5'), 3.50 (dd, 1H, J=7.93, 7.63, 10.68 Hz, H-5'), 3.41 (s, 3H, $CH_3$);
HRMS ESI (−) calcd. m/z $C_{12}H_{15}IN_5O_4^-$ [M−H]⁻: 420.01741, found: 420.01758.

guanosine 5'-deoxy-5'-thioguanosine-5'-monophosphorothiolate (FIG. 2, No. 7)

To a suspension of 5'-deoxy-5'-iodoguanosine (FIG. 2, nr 3) (2.0 g, 5.1 mmol) in 100 mL of DMF:$H_2O$ mixture (1:1, v/v) trisodium thiophosphate (4.6 g, 25.5 mmol) was added. The reaction mixture was stirred for 24 h at room temperature. Precipitate was removed by filtration, the filtrate was evaporated under reduced pressure. The residue was dissolved in 50 mL of water and the excess of trisodium thiophosphate was precipitated by addition of 100 mL of methanol. After separation, the crude product was purified by ion exchange chromatography on Sephadex. The product was freeze-dried. Yield 1.9 g, (64%). $t_R$ (B)=4.24 min;
¹H NMR (400 MHz, $D_2O$) δ ppm 8.05 (s, 1H, H-8), 5.89 (d, 1H, J=5.73 Hz, H-1'), 4.85 (dd, 1H, J=5.48 Hz, H-2'), 4.51 (2d, 1H, J=4.98, 4.23 Hz, H-3'), 4.33-4.39 (m, 1H, H-4'), 3.16-3.08 (m, 2H, Hz, H-5'); ³¹P NMR (162 MHz, $D_2O$) δ ppm 15.42 (s, 1P);
HRMS ESI (−) calcd. m/z $C_{10}H_{13}N_5O_7PS^-$ [M−H]⁻: 378.02788, found: 378.02828.

guanosine 5'-deoxy-5'-thio-7-methylguanosine-5'-monophosphorothiolate (FIG. 2, No. 8)

To a suspension of 5'-deoxy-5'-iodo-7-methylguanosine (FIG. 2, no. 6) (2.0 g, 4.92 mmol) in 100 mL of DMF trisodium thiophosphate (4.43 g, 24.6 mmol) was added. The reaction mixture was stirred for 48 h at room temperature. Precipitate was removed and the filtrate was evaporated under reduced pressure. The residue was dissolved in 50 mL of water and the excess of trisodium thiophosphate was precipitated by addition of methanol (100 mL). After separation, the crude product was purified by ion exchange chromatography on Sephadex. The product was freeze-dried. Yield 1.55 g, (53%). $t_R$ (B)=4.64 min;
¹H NMR (400 MHz, $D_2O$) δ ppm 7.85 (s, 1H, H-8), 5.89 (d, 1H, J=3.74 Hz, H-1'), 4.78-4.75 (m, 1H, H-2'), 4.43-4.39 (m, 2H, H-3', H-4'), 4.09 (s, 3H, $CH_3$), 3.08-2.94 (m, 2H, Hz, H-5'); ³¹P NMR (162 MHz, $D_2O$) δ ppm 14.45 (s, 1P);
HRMS ESI (−) calcd. m/z $C_{11}H_{15}N_5O_7PS^-$ [M−H]⁻: 392.04353, found: 392.04378.

General Procedure of Synthesis of guanosine 5'-deoxy-5'-thioguanosine-5'-monophosphorothiolate imidazolides (FIG. 2, No. 9, 10)

An appropriate starting compound (nucleotide TEA salt) (1 mmol), was mixed with imidazole (10 mmol) and 2,2'-dithiodipyridine (3 mmol) in DMF (to the nucleotide concentration of 0.15 M). Next, triethylamine (3 mmol) and triphenylphosphine (3 mmol) were added, and the mixture was stirred for 24 h at room temperature. Addition of an anhydrous solution of $NaClO_4$ (4 mmol for each phosphate moiety) in dry acetone (volume 10× greater than the DMF added) resulted in precipitation of the product off the reaction mixture. After cooling to 4° C. the precipitate was filtered off, washed with cold, dry acetone and dried in vacuum over $P_4O_{10}$.

guanosine 5'-deoxy-5'-thioguanosine-5'-monophosphorothiolate imidazolide (FIG. 2, No. 9)

Guanosine 5'-deoxy-5'-thioguanosine-5'-monophosphorothioate imidazolide (FIG. 2, no. 9) (352 mg, 0.75 mmol, 89%) was obtained starting from 5'-deoxy-5'-thioguanosine-5'-monophosphorothioate (FIG. 2, no. 7) (500 mg, 0.86 mmol) following the general procedure. $t_R$ (B)=8.27 min;
³¹P NMR (162 MHz, $D_2O$) δ ppm 11.69 (m, 1P);
HRMS ESI (−) calcd. m/z for $C_{13}H_{15}N_7O_6PS^-$ [M−H]⁻: 428.05476, found 428.05452.

5'-deoxy-5'-thioguanosine-7-methylguanosine-5'-monophosphorothiolate imidazolide (FIG. 2, No. 10)

5'-deoxy-5'-thioguanosine-7-methylguanosine-5'-monophosphorothioate imidazolide (FIG. 2, no. 10) (321 mg, 0.69 mmol, 82%) was obtained starting from 5'-deoxy-5'-thio-7-methylguanosine-5'-monophosphorothioate (FIG. 2, no. 8) (500 mg, 0.84 mmol) following the general procedure. $t_R$ (B)=8.39 min;

HRMS ESI (−) calcd. m/z for $C_{14}H_{17}N_7O_6PS^-$ [M−H]$^-$: 442.07041, found 442.07070.

Guanosine 5'-deoxy-5'-thioguanosine-5'-diphosphorothiolate (FIG. 2, No. 11)

Guanosine 5'-deoxy-5'-thioguanosine-5'-monophosphorothioate imidazolide (FIG. 2, no. 9) (100 mg, 0.22 mmol) was dissolved in anhydrous DMF (2 mL), and tris(triethylammonium) phosphate (100 mg, 0.26 mmol) was added, followed by addition of $ZnCl_2$ (235.84 mg, 1.76 mmol). Reaction progress was controlled with RP-HPLC. The reaction mixture was stirred at room temperature until the disappearance of the starting material. Then, the reaction was stopped by addition of an aqueous solution of EDTA (513.92 mg, 1.76 mmol, 50 mL) and neutralized with 1M $NaHCO_3$. Crude product was purified by ion exchange chromatography on DEAE-Sephadex and isolated as TEA salts. Yield: 108.5 mg (0.14 mmol, 65%);

HRMS ESI (−) calcd. m/z for $C_{10}H_{14}N_5O_{10}P_2S^-$ [M−H]$^-$: 457.99421, found 457.99481.

5'-deoxy-5'-thioguanosine-7-methylguanosine-diphosphate (FIG. 2, No. 12)

5'-deoxy-5'-thioguanosine-7-methylguanosine-5'-monophosphorothioate imidazolide (FIG. 2, no. 10) (100 mg, 0.21 mmol) was dissolved in anhydrous DMF (2 mL), and tris(triethylammonium)-phosphate (100 mg, 0.26 mmol) was added, followed by addition of $ZnCl_2$ (224.54 mg, 1.68 mmol). Reaction progress was controlled with RP-HPLC. The reaction mixture was stirred at room temperature until the disappearance of the starting material. Then, the reaction was stopped by addition of an aqueous solution of EDTA (490.56 mg, 1.68 mmol, 50 mL) and neutralized with 1M $NaHCO_3$. Crude product was purified by ion exchange chromatography on DEAE-Sephadex and isolated as TEA salts. Yield: 91 mg (0.12 mmol, 54%), $t_R$ (B)=5.07 min, $^1$H NMR (400 MHz, $D_2O$) δ ppm 8.11 (s, 1H, H-8 slowly exchangeable), 5.97 (d, 1H, J=3.91 Hz, H-1'), 4.50, 4.49 (2d, 1H, J=5.09 Hz, H-2'), 4.41 (q, 1H, J=5.48, 5.09 Hz, H-3'), 4.07 (s, 3H, $CH_3$), 3.34-3.13 (m, 3H, H-4', H-5'); $^{31}$P NMR (162 MHz, $D_2O$) δ ppm 6.71 (d, 1P, J=30.81 Hz), 8.21 (d, 1P, J=30.81 Hz);

HRMS ESI calcd. m/z for $C_{11}H_{16}N_5O_{10}P_2S$—[M−H]$^-$: 472.00986, found 472.00967.

guanosine 5'-deoxy-5'-thio-7-methylguanosine-2'-diphosphorothiolate (FIG. 2, No. 13)

5'-deoxy-5'-thioguanosine-7-methylguanosine-5'-monophosphorothioate imidazolide (FIG. 2, no. 10) (100 mg, 0.21 mmol) was dissolved in anhydrous DMF (2 mL), and sodium thiophosphate (47 mg, 0.26 mmol) was added, followed by addition of $ZnCl_2$ (224.54 mg, 1.68 mmol). Reaction progress was controlled with RP-HPLC. The reaction mixture was stirred at room temperature until the disappearance of the starting material. Then, the reaction was stopped by addition of an aqueous solution of EDTA (490.56 mg, 1.68 mmol, 50 mL) and neutralized with 1M $NaHCO_3$. Crude product was purified by ion exchange chromatography on DEAE-Sephadex and the isolated TEA salt was used immediately in the coupling reaction. Yield: 110 mg (0.13 mmol, 64%);

HRMS ESI calcd. m/z for $C_{11}H_{16}N_5O_9P_2S_2^-$ [M−H]$^-$: 487.98702, found 487.98724.

Synthesis of 5'-S-Cap Analogs Via S-Alkylation

General Procedure

Nucleoside terminal thiophosphate TEA salt (1 equiv.) was suspended in DMSO (to concentration ca. 0.1-0.2 M). Then, DBU (1,8-diazabicyclo(5.4.0)undec-7-ene) (1 equiv.) and a derivative of 5'-iodoguanosine (1 equiv.) was added. The progress of the reaction was monitored by RP HPLC. The reaction was stopped after there was no signal from the terminal thiophosphate by addition of 1% acetic acid to pH=7, the reaction mixture was diluted with water and washed with ethyl acetate. Product was purified by ion exchange chromatography on DEAE-Sephadex and isolated as triethylammonium salt. The product was purified by semi-preparative RP-HPLC.

P1-(guanosin-5'-yl)-P2-(5'-deoxy-5'-thioguanosin-5'-yl) diphosphate-GppSG (FIG. 3, No. 19)

GppSG (207 mOD, 0.009 mmol, 24%) was obtained starting from GDPβS (FIG. 3, nr 14), (506 mOD, 0.042 mmol) following the general procedure. RP-HPLC: $t_R$ (A)=6.9 min;

$^1$H NMR (400 MHz, $D_2O$) δ ppm 7.96 (s, 1H), 7.81 (s, 1H), 5.77 (d, 1H, J=5.48 Hz), 5.70 (d, 1H, J=5.87 Hz), 4.80-4.70 (m, 2H, overlapped with water signal), 4.64 (t, 1H, J=5.48 Hz), 4.43 (t, 1H, t, J=3.91 Hz), 4.37 (t, 1H, J=3.91 Hz), 4.30-4.15 (m, 4H), 3.30-3.13 (m, 2H);

$^{31}$P NMR (162 MHz, $D_2O$) δ ppm 7.63 (d, 1P, J=32.28, 12.5 Hz), -12.02 (d, 1P, J=30.81 Hz); HRMS ESI (−) calcd. m/z for $C_{20}H_{25}N_{10}O_{14}P_2S^-$ [M−H]$^-$: 723.07531, found 723.07546.

P1-(7-methyl-guanosin-5'-yl)-P2-(5'-deoxy-5'-thioguanosin-5'-yl) diphosphate-m$^7$GppSG (FIG. 3, No. 21)

m$^7$GppSG (1028 mOD, 0.045 mmol, 9%) was obtained starting from m$^7$GDPβS (FIG. 3, No. 17, 5830 mOD, 0.51 mmol)) following the general procedure. RP-HPLC: $t_R$ (A)=5.9 min;

$^1$H NMR (400 MHz, $D_2O$) δ ppm 8.98 (s, 1H, H-8 m$^7$G), 7.87 (s, 1H, H-8 G), 5.88 (d, 1H, J=2.0 Hz, H-1' m$^7$G), 5.73 (d, 1H, J=5.7 Hz, H-1' G), 4.69 (t, 1H, J=5.5 Hz, H-2' G), 4.51 (bs., 1H, H-2' m$^7$G), 4.32-4.44 (m, 5H, H-3' G, H-3' m$^7$G, H-4' G, H-4' m$^7$G, H-5' m$^7$G), 4.24 (dd, 1H, J=11.3, 5.4 Hz, H5'' m$^7$G), 4.04 (s, 3H, $CH_3$), 3.24-3.41 (m, 2H, H5', 5'' G);

$^{31}$P NMR (162 MHz, $D_2O$) δ ppm 7.38 (dt, 1P, J=29.0, 11.5 Hz), -12.00 (d, 1P, J=32.23 Hz); HRMS ESI (−) calcd. m/z for $C_{21}H_{27}N_{10}O_{14}P_2S^-$ [M−H]$^-$: 737.09096, found 737.09052.

P1-(7-methyl-5'-deoxy-5'-thioguanosin-5'-yl)-P2-guanosin-5'-yl diphosphate-m$^7$GSppG (FIG. 3, No. 23)

m$^7$GSppG (1660 mOD, 0.073 mmol, 35%) was obtained starting from GDPβS (FIG. 3, No. 14; 2532 mOD, 0.21 mmol) following the general procedure. RP-HPLC: $t_R$ (A)=7.75 min;

$^1$H NMR (400 MHz, $D_2O$) δ ppm 7.99 (s, 1H, H-8 G), 5.83 (d, 1H, J=4.2 Hz, H-1' m$^7$G), 5.80 (d, 1H, J=6.0 Hz, H-1' G), 4.65-4.70 (2H, m, H-2' G, H-2' m$^7$G), 4.45 (t, 1H, J=4.1 Hz, H-3' G), 4.19-4.41 (5H, m, H-3' m$^7$G, H-4' G, H-4' m$^7$G, H5', 5'' G), 4.05 (s, 3H, $CH_3$), 3.35-3.43 (m, 2H, H5', 5'' m$^7$G);

³¹P NMR (162 MHz, D₂O) δ ppm 7.32 (dt, 1P, J=29.0, 11.0 Hz), -11.84 (d, 1P, J=29.00 Hz); HRMS ESI (−) calcd. m/z for $C_{21}H_{27}N_{10}O_{14}P_2S^-$ [M−H]⁻: 737.09096, found 737.09146.

P1-(guanosin-5'-yl)-P3-(5'-deoxy-5'-thioguanosin-5'-yl) trifphosphate—GpppSG (FIG. 3, No. 20)

GpppSG (1149 mOD, 0.051 mmol, 51%) was obtained starting from GTP$_\gamma$S (FIG. 3, No. 15; 1233 mOD, 0.10 mmol) following the general procedure. RP-HPLC: $t_R$ (A)=5.50 min;

¹H NMR (400 MHz, D₂O) δ ppm 8.02 (s, 1H, H-8 G), 7.90 (s, 1H, H-8 G), 5.82 (d, 1H, J=6.0 Hz, H-1' G), 5.78 (d, 1H, J=6.2 Hz, H-1' G), 4.84 (t, 1H, J=5.7 Hz, H-2' G), 4.74 (t, 1H, J=5.7 Hz, H-2' G), 4.52 (t, 1H, J=4.2 Hz, H-3' G), 4.47 (t, 1H, J=4.3 Hz, H-3' G), 4.30-4.38 (m, 2H, H-4', 5' G), 4.27 (m, 2H, H-4', 5" G), 3.25-3.35 (m, 2H, H5', 5" G);

³¹P NMR (162 MHz, D₂O) δ ppm 8.21 (dt, 1P, J=27.00, 13.3 Hz), -11.34 (d, 1P, J=19.30 Hz), -23.78 (dd, 1P, J=27.00, 19.30 Hz);

HRMS ESI (−) calcd. m/z for $C_{20}H_{26}N_{10}O_{17}P_3S^-$ [M−H]⁻: 803.04164, found 803.04135.

P1-(7-methyl-5'-deoxy-5'-thioguanosin-5'-yl)-P3-guanosin-5'-yl triphosphate-m⁷GSpppG (FIG. 3, No. 24)

m⁷GSpppG (729 mOD, 0.032 mmol, 13%) was obtained starting from GTP$_\gamma$S (FIG. 3, No. 15; 3000 mOD, 0.25 mmol) following the general procedure. RP-HPLC: $t_R$ (A)=5.36 min;

¹H NMR (400 MHz, D₂O) δ ppm 8.92 (s, 1H, H-8 m⁷G), 7.96 (s, 1H, H-8 G), 5.78 (d, 1H, J=4.30 Hz, H-1' m⁷G), 5.74 (d, 1H, J=5.87 Hz, H-1' G), 4.63 (m, 2H, H-2' G, H2' m⁷G), 4.48 (dd, 1H, J=4.43, 3.52 Hz, H-3' m⁷G), 4.36-4.26 (m, 4H, H-3' G, H-4' G, H-4' m⁷G, H-5' G), 4.24-4.19 (m, 1H, H-5" G), 4.00 (s, 3H, CH₃), 3.33-3.24 (2H, m, H-5', 5" m⁷G);

³¹P NMR (162 MHz, D₂O) δ ppm 7.57 (d, 1P, J=27.88 Hz), -11.68 (d, 1P, J=20.54 Hz), -24.00 (dd, 1P, J=29.35, 22.01 Hz);

HRMS ESI (−) calcd. m/z for $C_{21}H_{28}N_{10}O_{17}P_3S^-$ [M−H]⁻ 817.05729, found 817.05494.

P1-(7-methyl-guanosin-5'-yl)-P3-(5'-deoxy-5'-thio-guanosin-5'-yl) triphosphate-m⁷GpppSG (FIG. 3, No. 22)

m⁷GpppSG (1582 mOD, 0.07 mmol, 32%) was obtained starting from m⁷GTP$_\gamma$S (FIG. 3, No. 18; 2616 mOD, 0.23 mmol) following the general procedure. RP-HPLC: $t_R$ (A)=6.06 min;

¹H NMR (400 MHz, D₂O) δ ppm 9.02 (s, 1H, H-8 m⁷G), 7.87 (s, 1H, H-8 G), 5.84 (d, 1H, J=3.52 Hz, Ht m⁷G), 5.70 (d, 1H, J=6.65 Hz, H-1' G), 4.80-4.67 (m, 1H, H-2' G), 4.52 (t, 1H, J=4.30 Hz, H-2' m⁷G), 4.41 (dd, 2H, J=4.70, 4.30 Hz, H3' G, H3' m⁷G), 4.38-4.30 (m, 2H, H-4' G, H-4' m⁷G), 4.36-4.31 m, 2H, H5' m⁷G), 4.02 (s, 3H, CH₃), 3.30-3.20 (m, 2H, J=12.6, 6.3 Hz, H5', 5" G);

³¹P NMR (162 MHz, D₂O) δ ppm 7.66 (d, 1P, J=29.35 Hz), -11.73 (d, 1P, J=22.01 Hz), -23.95 (dd, 1P, J=22.01, 27.88 Hz);

HRMS ESI (−) calcd. m/z for $C_{21}H_{28}N_{10}O_{17}P_3S^-$ [M−H]⁻: 817.05729, found 817.05748.

P1-(2'-O-methyl-7-methyl-5'-deoxy-5'-thioguanosin-5'-yl)-P3-guanosin-5'-yl triphosphate-m$_2^{7,2'\text{-}O}$GSpppG (FIG. 3, No. 26)

m$_2^{7,2'\text{-}O}$GSpppG (140 mOD, 0.006 mmol, 5%) was obtained starting from GTP$_\gamma$S (FIG. 3, No. 15; 1500 mOD, 0.12 mmol) following the general procedure. RP-HPLC: $t_R$ (A)=7.89 min;

¹H NMR (400 MHz, D₂O) δ ppm 7.93 (s, 1H, G), 5.81 (d, 1H, J=3.91 Hz, H-1' m⁷G), 5.72 (d, 1H, J=6.26 Hz, H-1' G), 4.65 (t, 1H, J=5.48 Hz, H-2' m⁷G), 4.43-4.40 (m, 1H, H-2', G, H-3' m⁷G), 4.32-4.18 (m, 6H, H-3' G, H-4', H-5', G, m⁷G), 4.01 (s, 3H, CH₃), 3.52 (s, 3H, OCH₃);

³¹P NMR (162 MHz, D₂O) δ ppm 7.35 (d, 1P, J=26.41 Hz), -11.68 (d, 1P, J=19.07 Hz), -24.02, -24.18 (2d, 1P, J=26.41, 19.07 Hz);

HRMS ESI (−) calcd. m/z for $C_{22}H_{30}N_{10}O_{17}P_3S^-$ [M−H]⁻ 831.07294, found 831.07477.

P1-(7-methyl-5'-deoxy-5'-thioguanosin-5'-yl)-P3-guanosin-5'-yl-2,3-methylenotriphosphate-m⁷GSppCH₂pG (FIG. 3, No. 25)

m⁷GSppCH₂pG (353 mOD, 0.016 mmol, 27%) was obtained starting from m⁷GpCH₂ppγS (FIG. 3, no. 16; 717 mOD, 0.06 mmol) following the general procedure. RP-HPLC: $t_R$ (A)=6.36 min;

¹H NMR (400 MHz, D₂O) δ ppm 9.03 (s, 1H, H-8, m⁷G), 8.17 (s, 1H, G), 5.83 (d, 1H, J=4.30 Hz, H-1' m⁷G), 5.78 (d, 1H, J=4.48 Hz, H-1' G), 4.70-4.66 (m, 2H, H-2' m⁷G, H-2', G), 4.46 (d, 1H, J=3.91, 5.09 Hz, H-3', G), 4.38-4.33 (m, 2H, H-3', m⁷G, H-4', G), 4.32-4.28 (m, 1H, H-4', m⁷G), 4.26-4.20 (m, 1H, H-5', G), 4.19-4.13 (m, 1H, H-5" G), 4.02 (s, 3H, CH₃), 3.34-3.22 (m, 4H, H-5', G, m⁷G); ³¹P NMR (162 MHz, D₂O) δ ppm ³¹P NMR (162 MHz, D₂O) δ ppm 17.03 (d, 1P, J=10.27 Hz), 7.47-6.97 (m, 2P);

HRMS ESI (−) calcd. m/z for $C_{22}H_{30}N_{10}O_{16}P_3S^-$ [M−H]⁻ 815.07803, found 815.07923.

Synthesis of 5'-S-Cap Analogs Via Imidazolides

General Procedure

5'S-GMP-Im, (FIG. 2, no. 9) (Na salt, 50 mg, 0.11 mmol) and appropriate diphosphate (1 mmol): m$_2^{7,2'\text{-}O}$GDP (FIG. 4, No. 28), m⁷GpCH₂p (FIG. 4, No. 27), m⁷-5'S GDP (FIG. 2, no. 12), m⁷GSppβS (FIG. 2, no. 13) or m⁷GDPβS (FIG. 3, No. 17) were suspended in anhydrous DMF (1.0 mL) followed by addition of anhydrous ZnCl₂ (95 mg, 10 eq, 0.7 mmol). The reaction mixture was vigorously shaken until the reagents dissolved. The reaction progress was monitored by RP-HPLC. After completion (24 h), appropriate amount of EDTA solution (Na₂EDTA, 237 mg, 0.7 mmol) was added, pH was adjusted to 6 with solid NaHCO₃, followed by purification of the crude product by ion exchange chromatography by DEAE-Sephadex and isolated as TEA salts (or directly purified by preparative HPLC). The products were then additionally purified by RP-HPLC.

P1-(2'-O-methyl-7-methyl-guanosin-5'-yl)-P3-(5'-deoxy-5'-thioguanosin-5'-yl) triphosphate-m$_2^{7,2'\text{-}O}$GpppSG (FIG. 4, No. 38)

m$_2^{7,2'\text{-}O}$GpppSG (122 mOD, 0.005 mmol, 6%) was obtained starting from m$_2^{7,2'\text{-}O}$GDP (FIG. 4, No. 28; 912 mOD, 0.08 mmol) following the general procedure. RP-HPLC: $t_R$ (A)=6.29 min;

¹H NMR (400 MHz, D₂O) δ ppm 9.00 (s, 1H, H-8 m⁷G), 7.88 (s, 1H, G), 5.87 (d, 1H, J=2.74 Hz, H-1' m⁷G), 5.69 (d, 1H, J=6.65 Hz, H-1' G), 4.64 (t, 1H, J=5.48 Hz, H-2' m⁷G), 4.48 (dd, 1H, J=4.48 Hz, H-2', G), 4.43-4.38 (m, 2H, H-3', G, H-3' m7G), 4.36-4.32 (m, 1H, H-4', G), 4.30-4.26 (m, 1H, H-4', m⁷G), 4.25-4.16 (m, 2H, H-5', G), 4.03 (s, 3H, CH3), 3.53 (s, 3H, OCH₃), 3.30-3.22 (m, 2H, H-5' m⁷G);

³¹P NMR (162 MHz, D₂O) δ ppm 7.68 (d, 1P, J=27.88 Hz), -11.68 (d, 1P, J=20.54 Hz), -23.78, -23.94 (2d, 1P, J=27.88, 19.07 Hz);

HRMS ESI (-) calcd. m/z for C₂₂H₃₀N₁₀O₁₇P₃S⁻ [M-H]⁻ 831.07294, found 831.07350.

P1-(7-methyl-5'-deoxy-5'-tioguanozyn-5'-yl)-P3-guanosin-5'-yl 1,2-methylenetriphosphate-m⁷GpCH₂ppSG (FIG. 4, No. 37)

m⁷GpCH₂ppSG (1002 mOD, 0.044 mmol, 25%) was obtained starting from m⁷GpCH₂p (FIG. 4, no. 27; 2052 mOD, 0.18 mmol) and 5'-S-GMP-Im (122 mg, 0.27 mmol) following the general procedure. RP-HPLC: $t_R$ (A)=6.26 min, ¹H NMR (400 MHz, D₂O) δ ppm 9.31 (s, 1H, H-8, m⁷G), 8.02 (s, 1H, G), 5.90 (d, 1H, J=3.13 Hz, H-1' m⁷G), 5.75 (d, 1H, J=5.87 Hz, H-1' G), 4.80-4.70 (m, 2H, overlapped with solvent signal, H-2' m⁷G, H-2', G), 4.58 (dd, 1H, J=3.91, 3.48 Hz, H-3', G), 4.48 (t, 1H, H-3', m⁷G), 4.40 (dd, 1H, J=3.91, 4.06, H-4', G), 4.37-4.29 (m, 3H, H-4', m⁷G, H-5', G), 4.19-4.13 (m, 2H, H-5', G), 4.03 (s, 3H, CH₃), 3.30-3.19 (m, 2H, H-5', G, m⁷G), 2.40 (t, 2H, J=20.35 Hz, CH₂);

³¹P NMR (162 MHz, D₂O) δ ppm 17.11 (d, 1P, J=8.80 Hz), 7.64-6.76 (m, 2P);

HRMS ESI (-) calcd. m/z for C₂₂H₃₀N₁₀O₁₆P₃S⁻ [M-H]⁻ 815.07803, found 815.07906.

P1-(7-methyl-5'-deoxy-5'-thioguanozy-5'-yl)-P3-(5'-deoxy-5'-thioguanosin-5'-yl) triphosphate-m⁷GSpppSG (FIG. 4, No. 32)

m⁷GSpppSG (768 mOD, 32 mg, 0.028 mmol, 40%) was obtained starting from m⁷-5'S-GDP (57 mg, 0.07 mmol) and 5'S-GMP-Im (50 mg, 0.11 mmol) following the general procedure. RP-HPLC: $t_R$ (A)=6.80 min;

¹H NMR (400 MHz, D₂O) δ ppm 8.38 (s, 1H, H-8 m⁷G slowly exchangeable), 7.84 (s, 1H, G), 5.78 (d, 1H, J=4.70 Hz, H-1' m⁷G), 5.69 (d, 1H, J=6.65 Hz, H-1' G), 4.64 (t, 1H, J=4.70 Hz, H-2' m⁷G), 4.40, 4.39 (2d, 1H, J=2.74, 3.52, 4.40 Hz, H-3', G), 4.36-4.29 (m, 3H, H-4' G, H-5', G), 3.99 (s, 3H, CH₃), 4.37-4.28 (m, 3H, H-4', H-5', m⁷G);

³¹P NMR (162 MHz, D₂O) δ ppm 7.74 (t, 2P, J=27.88), -24.61 (t, 1P, J=29.35 Hz);

HRMS ESI (-) calcd. m/z for C₂₁H₂₈N₁₀O₁₆P₃S₂⁻ [M-H]⁻ 833.03445, found 833.03550.

P1-(7-methyl-5'-deoxy-5'-thioguanosin-5'-yl)-P3-guanosin-5'-yl 2-thiotriphosphate m⁷GSpp$_s$pG D1/D2 (FIG. 4, No. 30, 31, respectively)

m⁷GSpp$_s$pG (1080 mOD, 45 mg, 0.039 mmol, 56%) was obtained as a mixture of diastareoisomers D1/D2 starting from m⁷GSppβS (56 mg, 0.07 mmol) and 5'S-GMP-Im (50 mg, 0.11 mmol) following the general procedure. Diastereoisomers were separated using RP-HPLC and isolated as ammonium salts. D1 (FIG. 4, No. 30) (438 mOD, 18 mg, 0.016 mmol, 23%) RP-HPLC: $t_R$ (A)=6.56 min;

¹H NMR (400 MHz, D₂O) δ ppm 8.98 (s, 1H, H-8, m⁷G), 8.08 (s, 1H, G), 5.82 (d, 1H, J=4.27 Hz, H-1' m⁷G), 5.77 (d, 1H, J=5.80 Hz, H-1' G), 4.67-4.65 (m, 2H, H-2' m⁷G, H-2', G), 4.49-4.47 (m, 1H, H-3', G), 4.39-4.35 (m, 1H, H-3', m⁷G, H-4', G), 4.33-4.23 (m, 3H, H-4', m⁷G, H-5', G), 4.02 (s, 3H, CH₃), 3.38-3.25 (m, 2H, H-5', m⁷G);

³¹P NMR (162 MHz, D₂O) δ ppm 29.18 (dd, 1P, J=34.83, 27.37 Hz), 6.96 (dt, 1P, J=34.83, 12.44 Hz), -12.37 (d, 1P, J=27.37 Hz);

HRMS ESI (-) calcd. m/z for C₂₁H₂₈N₁₀O₁₆P₃S₂⁻ [M-H]⁻: 833.03445, found 833.03549.

D2 (FIG. 4, No. 31): m⁷GSpp$_s$pG D2 (380 mOD, 16 mg, 0.014 mmol, 20%) RP-HPLC: $t_R$ (A)=6.71 min;

¹H NMR (400 MHz, D₂O) δ ppm 8.98 (s, 1H, H-8, m⁷G), 8.14 (s, 1H, G), 5.82 (d, 1H, J=4.27 Hz, H-1' m⁷G), 5.77 (d, 1H, J=5.49 Hz, H-1' G), 4.69-4.65 (m, 2H, H-2' m⁷G, H-2', G), 4.49-4.45 (m, 1H, H-3', G), 4.40-4.35 (m, 1H, H-3', m⁷G, H-4', G), 4.34-4.21 (m, 3H, H-4', m⁷G, H-5', G), 4.03 (s, 3H, CH₃), 3.39-3.24 (m, 2H, H-5', m⁷G);

³¹P NMR (162 MHz, D₂O) δ ppm 29.44-28.67 (m, 1P), 7.17-6.54 (m, 1P), -12.09-(-12.72) (m, 1P);

HRMS ESI (-) calcd. m/z for C₂₁H₂₈N₁₀O₁₆P₃S₂⁻ [M-H]⁻: 833.03445, found 833.03606.

P1-(7-methyl-5'-deoxy-5'-thioguanosin-5'-yl)-P3-(5'-deoxy-5'-thioguanosin-5'-yl) 2-tiotriphosphate-m⁷GSpp$_s$pSG D1/D2 (FIG. 4, No. 33, 34, Respectively)

m⁷GSpp$_s$pSG (942 mOD, 39 mg, 0.003 mmol, 48%) was obtained as a mixture of diastareoisomers D1/D2 starting from m⁷GSppβS (56 mg, 0.07 mmol) and 5'S-GMP-Im (50 mg, 0.11 mmol) following the general procedure. Diastereoisomers were separated using RP-HPLC and isolated as ammonium salts. D1 (FIG. 4, No. 33) (510 mOD, 21 mg, 0.018 mmol, 26%) RP-HPLC: $t_R$ (A)=7.53 min;

¹H NMR (400 MHz, D₂O) δ ppm 9.00 (s, 1H, H-8, m⁷G), 7.99 (s, 1H, G), 5.83 (d, 1H, J=4.27 Hz, H-1' m⁷G), 5.75 (d, 1H, J=6.10 Hz, H-1' G), 4.79-4.68 (m, 2H, overlapped with solvent signal, H-2' m⁷G, H-2', G), 4.44 (dd, 1H, J=4.58 Hz, H-3', G), 4.41-4.33 (m, 3H, H-3', m⁷G, H-4', G, m⁷G), 4.03 (s, 3H, CH₃), 3.39-3.26 (m, 4H, H-5', G, m⁷G);

³¹P NMR (162 MHz, D₂O) δ ppm 28.25 (t, 1P, J=34.83 Hz), 7.31-6.74 (m, 2P);

HRMS ESI (-) calcd. m/z for C₂₁H₂₈N₁₀O₁₅P₃S₃⁻ [M-H]⁻: 849.01161, found 849.01213.

D2 (FIG. 4, No. 34) (274 mOD, 11 mg, 0.0098 mmol, 14%), RP-HPLC: $t_R$ (A)=7.62 min;

¹H NMR (400 MHz, D₂O) δ ppm 8.99 (s, 1H, H-8, m⁷G), 8.04 (s, 1H, G), 5.83 (d, 1H, J=4.58 Hz, H-1' m⁷G), 5.75 (d, 1H, J=6.10 Hz, H-1' G), 4.78-4.66 (m, 2H, overlapped with solvent signal, H-2' m⁷G, H-2', G), 4.46-4.42 (m, 1H, H-3', G), 4.41-4.34 (m, 3H, H-3', m⁷G, H-4', G, m⁷G), 4.04 (s, 3H, CH₃), 3.39-3.24 (m, 4H, H-5', G, m⁷G);

³¹P NMR (162 MHz, D₂O) δ ppm 28.29 (t, 1P, J=34.83 Hz), 7.32-6.68 (m, 2P);

HRMS ESI (-) calcd. m/z for C₂₁H₂₈N₁₀O₁₅P₃S₃⁻ [M-H]⁻: 849.01161, found 849.01217.

P1-(7-methyl-guanosin-5'-yl)-P3-(5'-deoxy-5'-thio-guanosin-5'-yl) 2-thiotriphosphate-m⁷Gpp$_s$pSG D1/D2 (FIG. 4, No. 35, 36, Respectively)

m⁷GppspSG (1941 mOD, 0.086 mmol, 28%) was obtained as a mixture of diastareoisomers D1/D2 starting from m⁷GDPβS (3492 mOD, 0.31 mmol) and 5'-S-GMP-Im (5550 mOD, 0.46 mmol) following the general procedure. Diastereoisomers were separated using RP-HPLC and isolated as ammonium salts. D1 (FIG. 4, No. 35): (888 mOD, 0.039 mmol, 13%) RP-HPLC: $t_R$ (A)=7.12 min;

$^1$H NMR (400 MHz, D$_2$O) δ ppm 9.07 (s, 1H, H-8, m$^7$G), 7.95 (s, 1H, G), 5.88 (d, 1H, J=3.52 Hz, H-1' m$^7$G), 5.74 (d, 1H, J=6.26 Hz, H-1' G), 4.80-4.70 (m, 2H, H-2' m$^7$G, H-2', G overlapped with D2O signal), 4.56 (dd, 1H, J=4.70, 3.52 Hz, H-3', G), 4.47-4.40 (m, 2H, H-3', m$^7$G, H-4', G), 4.39-4.33 (m, 3H, H-4', m$^7$G, H-5', G), 4.03 (s, 3H, CH$_3$), 3.35-3.20 (m, 2H, H-5', m$^7$G);

$^{31}$P NMR (162 MHz, D$_2$O) δ ppm 29.00 (dd, 1P, J=33.75, 26.41 Hz), 6.98 (d, 1P, J=33.75, Hz), −12.56 (d, 1P, J=24.94 Hz);

HRMS ESI (−) calcd. m/z for C$_{21}$H$_{28}$N$_{10}$O$_{16}$P$_3$S$_2^-$ [M−H]$^-$: 833.03445, found 833.03514.

D2 (FIG. 4, No. 36): m$^7$GppspG D2 (1053 mOD, 0.046 mmol, 15%) RP-HPLC: $t_R$ (A)=7.42 min;

$^1$H NMR (400 MHz, D$_2$O) δ ppm 9.04 (s, 1H, H-8, m$^7$G), 7.95 (s, 1H, G), 5.85 (d, 1H, J=3.52 Hz, H-1' m$^7$G), 5.73 (d, 1H, J=6.26 Hz, H-1' G), 4.80-4.70 (m, 2H, H-2' m$^7$G, H-2', G overlapped with D$_2$O signal), 4.54 (dd, 1H, J=4.30, 3.91 Hz, H-3', G), 4.45 (t, 1H, J=5.09 Hz, H-3', m$^7$G), 4.43-4.40 (m, 1H, H-4', G), 4.39-4.32 (m, 3H, H-4', m$^7$G, H-5', G), 4.03 (s, 3H, CH$_3$), 3.37-3.21 (m, 2H, H-5', m$^7$G);

$^{31}$P NMR (162 MHz, D$_2$O) δ ppm 28.99 (dd, 1P, J=33.75, 26.41, 24.94 Hz), 6.94 (d, 1P, J=35.21, Hz), -12.48 (d, 1P, J=24.94 Hz);

HRMS ESI (−) calcd. m/z for C$_{21}$H$_{28}$N$_{10}$O$_{16}$P$_3$S$_2^-$ [M−H]$^-$: 833.03445, found 833.03494.

TABLE 4

Synthesised and studied new cap analogs are presented.

| Number | Compound | Structural formula | Chemical name |
|---|---|---|---|
| 12 | m$^7$GSpp | | 5'-deoxy-5'-thioguanosin-5'-7-methyloguanosine diphosphate |
| 21 | m$^7$GppSG | | P1-(7-methyl-guanosin-5-yl)-P2-(5-deoxy-5'-thioguanosin-5'-yl) diphosphate |
| 22 | m$^7$GpppSG | | P1-(7-methyl-guanosin-5'-yl)-P3-(5'-deoxy-5'-thioguanosin-5'-yl) triphosphate |
| 23 | m$^7$GSppG | | P1-(7-methyl-5'-deoxy-5'-thioguanosin-5'-yl)-P2-guanosin-5'-yl diphosphate |

TABLE 4-continued

Synthesised and studied new cap analogs are presented.

| Number | Compound | Structural formula | Chemical name |
|---|---|---|---|
| 24 | m⁷GSpppG | | P1-(7-methyl-5'-deoxy-5'-thioguanosin-5'-yl)-P3-guanosin-5'-yl triphosphate |
| 25 | m⁷GSppCH₂pG | | P1-(7-methyl-5'-deoxy-5'-thioguanosin-5'-yl)-P3-guanosin-5'-yl 2,3-metylenetriphosphate |
| 26 | m⁷,²'ᴼGSpppG | | P1-(2'-O-methyl-7-methylo-5'-deoxy-5'-thioguanosin-5'-ylo)-P3-guanosin-5'-yl triphosphate |
| 30 | m⁷GSpp$_s$pG D1 | | P1-(7-methyl-5'-deoxy-5'-thioguanosin-5'-yl)-P3-guariosin-5'-yl 2-triphosphate D1 |
| 31 | m⁷GSpp$_s$pG D2 | | P1-(7-methyl-5'-deoxy-5'-thioguanosin-5'-yl)-P3-guanosin-5'-yl 2-triphosphate D2 |
| 32 | m⁷GSpppSG | | P1-(7-methyl-5'-deoxy-5'-thioguanosin-5'-yl)-P3-(5'-deoxy-5'-thioguanosin-5'-yl) triphosphate |

TABLE 4-continued

Synthesised and studied new cap analogs are presented.

| Number | Compound | Structural formula | Chemical name |
|---|---|---|---|
| 33 | m⁷GSpp$_s$pSG D1 | | P1-(7-methyl-5'-deoxy5'-thioguanosin-5'-yl)-P3-(5'-deoxy-5'-thioguanosin-5'-yl) 2-triphosphate D1 |
| 34 | m⁷GSpp$_s$pSG D2 | | P1-(7-methyl-5'-deoxy-5'-thioguanosin-5'-yl)-P3-(5'-deoxy-5'-thioguanosin-5'-yl) 2-triphosphate D2 |
| 35 | m⁷Gpp$_s$pSG D1 | | P1-(7-methyl-guanosin-5'-yl)-P3-(5'-deoxy-5'-thioguanosin-5'-yl) 2-triphosphate D1 |
| 36 | m⁷Gpp$_s$pSG D2 | | P1-(7-methyl-guanosin-5'-yl)-P3-(5'-deoxy-5'-thioguanosin-5'-yl) 2-triphosphate D2 |
| 37 | m⁷GpCH₂ppSG | | P1-(7-methyl-5'-deoxy-5'-thioguanosin-5'-yl)-P3-guanosin-5'-yl 1,2-metylenetriphosphate |
| 38 | m⁷,²'ᴼGpppSG | | P1-(2'-O-methyl-7-methyl-guanosin-5'-yl)-P3-(5'-deoxy-5'-htioguanosin-5'-yl) triphosphate |

Example 2. New Cap Analogs Characteristics

Test 1. The Susceptibility Study of Analogs to Degradation by DcpS Enzyme.

The aim of the test was to check if new 5'-thiophosphate cap analogs are hydrolyzed by human DcpS enzyme (hDcpS). Recombinant human protein encoding DcpS enzyme was expressed as described previously (Kowalska, Lewdorowicz et al. 2008). The susceptibility of new analogs to hDcpS hydrolysis is tested in 50 mM Tris-HCl buffer containing 200 mM KCl and 0.5 mM EDTA. Reaction mixture includes the tested cap analog (20 μM) and hDcpS enzyme (100 nM) in 400 μl of buffer. At the appropriate intervals 100 μl sample is collected from the reaction mixture. Sample is incubated at 98° C. for 2.5 min, and then cooled to 0° C. and analyzed on RP-HPLC under conditions described in general informations. In tests also commercially available inhibitor of DcpS was tested, the compound RG3039 (no. 000) (https://www.mda.org/quest/fda-approves-phase-1-clinical-trial-rg3039-sma), GppSG (no. 19), GpppSG (no. 20), as well m$^7$GpppG (no. 0) and m$^7$Gpp (no. 00) as controls. Exemplary results obtained are shown on FIG. 5 and Table 5.

Test 2. IC$_{50}$ Determination for Selected Inhibitors

The purpose of the test was to determine the concentration, wherein the given inhibitor inhibits DcpS activity to 50% of the maximal value in the particular conditions. The buffer in this test and in the test 1 is the same. Ten mixture reactions were prepared at the same time and each of them contained a m$^7$GMPF (60 μM), hDcpS enzyme (50 nM) and the tested compound in concentration range between 0-50 μM in 200 μl of buffer. After appropriate time, when 30% of substrate were converted into product without inhibitor, the reaction was stopped by mixing with 100 μl of ACN. Samples of 25 μl were taken for analysis, followed by mixing with 90 μl of TBDS-fluorescein solution of concentration 2.5 μM in DMSO and incubated for 60 min. Next, 100 μl of 200 mM HEPES buffer pH=7.0 was added to the samples and the fluorescence was measured as described in general information. Based on the results, dependence of inhibitor concentration vs. fluorescence were plotted and the IC$_{50}$ values were determined by fitting theoretical curve to data. Obtained results are presented in Table 5 and FIG. 5.

TABLE 5

IC$_{50}$ values and susceptibility for degradation by DcpS enzyme for selected compounds.

| No. | Compound | DcpS susceptibility | IC$_{50}$ [μM] |
|---|---|---|---|
| 0 | m$^7$GpppG | hydrolyzable | nd |
| 00 | m$^7$Gpp | resistant/inhibitor | 4.30 ± 0.78 |
| 000 | RG3039 | resistant/inhibitor | 0.041 ± 0.012 |
| 12 | m$^7$GSpp | resistant/inhibitor | 1.93 ± 0.38 |
| 19 | GppSG | hydrolyzable | above 100 |
| 20 | GpppSG | hydrolyzable | above 100 |
| 21 | m$^7$GppSG | hydrolyzable | nd |
| 22 | m$^7$GpppSG | hydrolyzable | nd |
| 23 | m$^7$GSppG | resistant/inhibitor | 2.81 ± 0.51 |
| 24 | m$^7$GSpppG | resistant/inhibitor | 0.84 ± 0.07 |
| 25 | m$^7$GSppCH$_2$pG | resistant/inhibitor | 6.25 ± 1.22 |
| 26 | m$^{7,2'O}$GSpppG | resistant/inhibitor | 12.57 ± 5.22 |
| 30 | m$^7$GSpp$_s$pG D1 | resistant/inhibitor | 0.23 ± 0.04 |
| 31 | m$^7$GSpp$_s$pG D2 | resistant/inhibitor | 0.17 ± 0.02 |
| 32 | m$^7$GSpppSG | resistant/inhibitor | 0.33 ± 0.09 |
| 33 | m$^7$GSpp$_s$pSG D1 | resistant/inhibitor | 0.26 ± 0.04 |
| 34 | m$^7$GSpp$_s$pSG D2 | resistant/inhibitor | 0.051 ± 0.008 |
| 35 | m$^7$Gpp$_s$pSG D1 | hydrolyzable | nd |

TABLE 5-continued

IC$_{50}$ values and susceptibility for degradation by DcpS enzyme for selected compounds.

| No. | Compound | DcpS susceptibility | IC$_{50}$ [μM] |
|---|---|---|---|
| 36 | m$^7$Gpp$_s$pSG D2 | hydrolyzable | nd |
| 37 | m$^7$GpCH$_2$ppSG | resistant/inhibitor | 5.67 ± 1.01 |
| 38 | m$^{7,2'O}$GpppSG | hydrolyzable | 72 ± 17 |

Test 3. Structure Determination of Human DcpS Enzyme (ΔN37hDcpS) in Complex with Analog No. 34 (m$^7$GSpp$_s$pSG D2)

The aim of this test was to study the mechanism of interactions of analog no. 34 with human DcpS enzyme. Recombinant human DcpS enzyme truncated at the N-terminus (ΔN37-residues Ala38 to Ser337) was obtained as described earlier (Singh et al. 2008). Crystallization by sitting drop vapor diffusion was performed using 0.2 uL of sample containing 0.1 M analog 34 and 7.3 mg/mL DcpS enzyme (incubated on ice for 15 min prior to crystallization setup) and 0.2 uL of reservoir solution. Complex crystals appeared in a mixture containing 29% PEG 4000 and 0.1M Tris.HCl pH 7.6 after about a week. To the drop containing crystal a mixture of reservoir solution and glycerol (1:1 v/v) was added and then the crystals were harvested and flash frozen in liquid nitrogen. The diffraction data were collected at 100K at synchrotron source (Beamline 14.1, Bessy II, Helmholtz-Zentrum Berlin, Germany) using a Dectris PILATUS 6M detector and then data were processed using XDS software (Kabsch 2010). The structure was solved by Molecular Replacement using Phaser software (McCoy, Grosse-Kunstleve et al. 2007) with a structure of DcpS bound to DG157493 inhibitor (pdb: 3BL9) (Singh, Salcius et al. 2008) as a search model. Ligand model and dictionary were generated using ProDRG (Schuttelkopf and van Aalten 2004). The model building and ligand fitting was performed in Coot software (Emsley & Cowtan 2004). The structure was refined using phenix.refine (Adams, Afonine et al. 2010).

Test 4. Susceptibility Study of Short RNA Molecules Comprising Cap Analogs at the 5' End to Degradation with the Dcp1/2 Enzyme.

The aim of this study was to check whether incorporation of selected 5'-phosphothioate cap analogs to 5' end of RNA could influence susceptibility of thus prepared transcripts towards Dcp1/2 decapping enzyme activity. *Schizosaccharomyces pombe* recombinant protein in the form of a heterodimer Dcp1/2 was obtained as described previously (Floor, Jones et al. 2010). The trancripts utilized in this assay were obtained by transcription in vitro using RNA SP6 polymerase (New England BioLabs). Annealed oligonucleotides: ATACGATTTAGGTGACAC-TATAGAAGAAGCGGGCATGCGGCCAGCCATAGCC-GATCA (SEQ ID NO.: 1), and TGATCGGCTATGGCTGGCCGCATGCCCGCTTCTTC-TATAGTGTCACCTAAATCGTAT (SEQ ID NO: 2) were used as a template in in vitro transcription, the oligonucleotides comprising the promoter sequence for SP6 polymerase (ATTTAGGTGACACTATAGA (SEQ ID NO: 3)) allow to obtain 35 nt long RNAs having a sequence of GAAGAAGCGGGCAUGCGGCCAGC-CAUAGCCGAUCA (SEQ ID NO: 4), however 5' end capped RNAs are 36 nt long. Typical in vitro transcription reaction was performed in volume 20 μl and was incubated in 40° C. for 2 hours and contained the following: 1U SP6 polymerase, 1 U RiboLock RNase Inhibitor (ThermoFisher Scientific), 0.5 mM ATP/CTP/UTP, 0.125 mM GTP, 1.25 mM dinucleotide cap analog and 0.1 µM template. Following 2 hours incubation, 1U DNase I (Ambion) was added to the reaction mixture and incubation was continued for 30 min in 37° C., after that EDTA was added to 25 mM final concentration. Obtained RNAs were purified using RNA Clean & Concentrator-25 (Zymo Research). Then the quality of the synthesized RNA was determined on a denaturating 15% polyacrylamide gel. The concentration of the RNA was in turn evaluated spectrophotometrically. The thus obtained RNA is characterized by substantial heterogeneity of the 3' end, hence to eliminate the problem, the obtained RNAs were incubated with DNAzyme 10-23 (TGATCGGCTAGGCTAGCTA-CAACGAGGCTGGCCGC (SEQ ID NO: 5)) which lead to obtaining RNA 25 nt long. RNA having a cap at the 5' end was 26 nt long. The reaction of cleaving the 3' ends was as follows: 1 µM of RNA was incubated with 1 µM of DNazyme 10-23 in a mixture containing 50 mM $MgCl_2$ and 50 mM Tris-HCl pH 8.0 for 1 hour in 37° C. (Coleman et al., 2004).

For enzymatic tests 20 ng of each RNA was used, which were incubated with 3.5 nM Dcp1/2 enzyme in buffer containing 50 mM Tris-HCl pH 8.0, 50 mM $NH_4Cl$, 0.01% NP-40, 1 mM DTT, and 5 mM $MgCl_2$. Reactions were performed at 37° C. in the final volume of 25 µl. The reaction was stopped after 0, 5, 15 and 30 min by adding an equal amount of a mixture of 5 M urea, 44% formamide, 20 mM EDTA, 0.03% bromophenol blue, 0.03% xylene cyanol. Reaction products were resolved on denaturing 15% polyacrylamide gels, after the electrophoretic separation was completed, the gel was stained with SYBR Gold (Invitrogen) and visualized using a Storm 860 PhosphorImager (GE Healthcare). Quantification of the obtained results was performed with ImageQuant software (Molecular Dynamics). Representative results of this assay were presented on FIG. 8, FIG. 9 and also in Table 6.

TABLE 6

Biological properties of mRNAs comprising selected cap analogs at the 5' end

| | capping efficiency[a] | Dcp1/2 susceptibility[b] | relative translation efficiency[c] |
|---|---|---|---|
| GpppG | 0.91 | 0 | 0.05 ± 0.01 |
| m[7]GpppG | 0.93 | 0.69 | 1.00 |
| $m_2^{7,2'\text{-}o}$GpppG | 0.84 | 0.52 | 1.56 ± 0.14 |
| $m_2^{7,2'\text{-}o}$Gpp$_s$pG D2 | 0.82 | 0.43 | 3.45 ± 0.42 |
| $m_2^{7,2'\text{-}o}$GSpppG | 0.70 | 0.07 | 1.73 ± 0.24 |
| $m_2^{7,2'\text{-}o}$GpppSG | 0.76 | 0.52 | 2.23 ± 0.31 |

[a]The data of FIG. 8 (time point 0') were used to calculate capping efficiency.
[b]The data of FIG. 8 were used to calculate susceptibility to Dcp1/2 activity, given as ratio of capped RNAs to a sum of uncapped and capped RNA at one time point 15 min and after normalization to 0' time for individual RNAs.
[c]Relative translational efficiency shows the average translation efficiency of Renilla luciferase mRNAs in biological triplicates after normalization to the values obtained for mRNA capped with m[7]GpppG at the 5' end.

Test 5. Study on the Effect of the Presence of Novel Cap Analogs on Translational Efficiency of mRNAs in Rabbit Reticulocyte Lysate.

The aim of this study was to check the effect of introducing novel cap analogs at the 5' end of mRNAs on translation efficiency. For this purpose series of *Renilla* luciferase encoding mRNAs, and differing in the cap structure at the 5' end were prepared. The transcripts used for this test were obtained by in vitro transcription reaction using SP6 RNA polymerase. As the template for the in vitro transcription a PCR product was used, prepared using primers ATTTAGGTGACACTATAGAACAGATCTCGAGCT-CAAGCTT (SEQ ID NO: 6) and GTTTAAACATT-TAAATGCAATGA (SEQ ID NO: 7) and the hRLuc-pRNA2 (A)128 plasmid (Williams et al. 2010). PCR reaction thus conducted allowed to introduce promoter sequence for SP6 polymerase upstream of the sequence encoding *Renilla* luciferase. The transcription reaction itself was similar to the short RNA synthesis described above (Test 4). The reaction was conducted for 2 hours in 20 µl in 40° C. and contained the following: 1U SP6 polymerase, 1 U RiboLock RNase Inhibitor (ThermoFisher Scientific), 0.5 mM ATP/CTP/UTP, 0.125 mM GTP, 1.25 mM dinucleotide cap analog and 100 µg of a template. Following 2 hours incubation, 1U DNase I (Ambion) was added and incubation was continued for 30 min in 37° C., after that EDTA was added to 25 mM final concentration. Obtained mRNAs were purified using NucleoSpin RNA Clean-up XS (Macherey-Nagel). Quality of the synthetized RNA was checked on a denaturing 15% polyacrylamide gel. The RNA concentrations were determined spectrophotometrically.

An in vitro translation reaction was performed in rabbit reticulocyte lysate (RRL, Promega) in conditions determined for cap-dependent translation (Rydzik et al., 2009). A typical reaction mixture (10 µl) contained: 40% RRL lysate, 0.01 mM mixture of amino acids (Promega), 1.2 mM $MgCl_2$, 170 mM potassium acetate and a *Renilla* luciferase encoding mRNA with an appropriate cap analog at the 5' end, the mixture being incubated in 37° C. for 1 hour. Four different concentrations of mRNAs: 0.1 ng/µl, 0.25 ng/µl, 0.5 ng/µl, 0.75 ng/µl were used in the experiment. Activity of synthesized luciferase was measured using Dual-Luciferase Reporter Assay System (Promega) in a microplate reader Synergy H1 (BioTek). Obtained results were analyzed in Origin (Gambit) software, and theoretical curve was fitted to experimental data, wherein the slope of obtained curve represents translation efficiency. Representative data were presented on FIG. 10, whereas average translation efficiency obtained for biological triplicates is presented in Table 6.

Test 6. Study on the Effect of the Presence of Novel Cap Analogs on Translational Efficiency of mRNAs in HeLa Cells.

Human cervical carcinoma HeLa cells were grown in DMEM (Gibco) supplemented with 10% FBS (Sigma-Aldrich), 1% penicillin/streptomycin (Gibco) and L-glutamine with a final concentration of 2 mM at 5% $CO_2$ and 37° C. A day before the planned experiment, $10^4$ cells suspended in 100 µl medium without antibiotics were seeded per each well of a 96-well plate. The cell transfection was as follows, 0.3 µl Lipofectamine MessengerMAX Transfection Reagent (Invitrogen), 0.1 µg mRNA and 10 µl Opti-MEM (Gibco) were added to each well. The transfections were conducted for 1 hour in an incubator. After transfection, cells were washed three times with PBS and supplemented with fresh medium without antibiotics. After 2, 3, 4.5, 6.5, 10.5 and 24 hours since the beginning of transfection, the cells were washed three times with PBS, lysed and luciferase activity was measured using Luciferase Reporter Assay System (Promega) employing Synergy H1 microplate reader (Exemplary data are shown on FIG. 11.

mRNA encoding firefly luciferase and having two repeats of β-globin 3'UTR and poly(A) tail of 128 adenines at the 3' end was used for transfection. This mRNA, comprising differen cap analogs at the 5' end was obtained by in vitro transcription. pJET_luc_128A plasmid digested with AarI (ThermoFisher Scientifics) was used as a template for the synthesis. Typical in vitro transcription reaction) was conducted for 2 hours in a volume of 20 µl in 40° C. and contained the following: 1 U SP6 polymerase, 1 U RiboLock RNase Inhibitor (ThermoFisher Scientific), 0.5 mM ATP/CTP/UTP, 0.125 mM GTP, 1.25 mM dinucleotide cap analog and 0.1 μg of the template. The following steps of mRNA preparation as described above in the case of *Renilla* luciferase encoding mRNA (Test 5). Additionally, after purification of the mRNA using NucleoSpin RNA Clean-up XS column the transcripts were ethanol precipitated in presence of 2 μg glycogen and sodium acetate, then dissolved in deionized water.

BIBLIOGRAPHY

Abrams, W. R. and J. A. Schiff (1973). "Studies of sulfate utilization by algae. II. An enzyme-bound intermediate in the reduction of adenosine-5'-phosphosulfate (APS) by cell-free extracts of wild-type *Chlorella* and mutants blocked for sulfate reduction." *Arch Mikrobiol* 94(1): 1-10.

Adams, P., P. Afonine, G. Bunkoczi, V. Chen, I. Davis, N. Echols, J. Headd, L. Hung, G. Kapral, R. Grosse-Kunstleve, A. McCoy, N. Moriarty, R. Oeffner, R. Read, D. Richardson, J. Richardson, T. Terwilliger and P. Zwart (2010). "PHENIX: a comprehensive Python-based system for macromolecular structure solution." *Acta Crystallographica Section D—Biological Crystallography* 66: 213-221.

Akagi, J. M. and L. L. Campbell (1962). "STUDIES ON THERMOPHILIC SULFATE-REDUCING BACTERIA III.: Adenosine Triphosphate-sulfurylase of *Clostridium nigrificans* and *Desulfovibrio desulfuricans*." *J Bacteriol* 84(6): 1194-1201.

Arakawa, H., M. Shiokawa, O. Imamura and M. Maeda (2003). "Novel bioluminescent assay of alkaline phosphatase using adenosine-3'-phosphate-5'-phosphosulfate as substrate and the luciferin-luciferase reaction and its application." *Anal Biochem* 314(2): 206-211.

Bail, S. and M. Kiledjian (2008). "DcpS, a general modulator of cap-binding protein-dependent processes?" *Rna Biology* 5(4): 216-219.

Barnes, S., R. Waldrop and A. S. Neighbors (1983). "Alkaline butanol extraction of bile salt and steroid sulfate esters: application to the assay of sulfotransferases." *Anal Biochem* 133(2): 470-475.

Butchbach, M. E. R., J. Singh, M. Þorsteinsdóttir, L. Saieva, E. Slominski, J. Thurmond, T. Andrésson, J. Zhang, J. D. Edwards, L. R. Simard, L. Pellizzoni, J. Jarecki, A. H. M. Burghes and M. E. Gurney (2010). "Effects of 2,4-diaminoquinazoline derivatives on SMN expression and phenotype in a mouse model for spinal muscular atrophy." *Human Molecular Genetics* 19(3): 454-467.

Contreras, R. and W. Fiers (1981). "Initiation of transcription by rna polymerase-II in permeable, SV40-infected or noninfected, CV1 cells—evidence for multiple promoters of SV40 late transcription." *Nucleic Acids Research* 9(2): 215-236.

Emsley, P. and K. Cowtan (2004). "Coot: model-building tools for molecular graphics." *Acta Crystallographica Section D—Biological Crystallography* 60: 2126-2132.

Floor, S., B. Jones, G. Hernandez and J. Gross (2010). "A split active site couples cap recognition by Dcp2 to activation." *Nature Structural & Molecular Biology* 17(9): 1096-U1099.

Grudzien, E., M. Kalak, J. Jemielity, E. Darzynkiewicz and R. E. Rhoads (2006). "Differential inhibition of mRNA degradation pathways by novel cap analogs." *Journal of Biological Chemistry* 281(4): 1857-1867.

Grudzien-Nogalska, E., J. Jemielity, J. Kowalska, E. Darzynkiewicz and R. E. Rhoads (2007). "Phosphorothioate cap analogs stabilize mRNA and increase translational efficiency in mammalian cells." *Rna-a Publication of the Rna Society* 13(10): 1745-1755.

Gu, M. G., C. Fabrega, S. W. Liu, H. D. Liu, M. Kiledjian and C. D. Lima (2004). "Insights into the structure, mechanism, and regulation of scavenger mRNA decapping activity." *Molecular Cell* 14(1): 67-80.

Jemielity, J., T. Fowler, J. Zuberek, J. Stepinski, M. Lewdorowicz, A. Niedzwiecka, R. Stolarski, E. Darzynkiewicz and R. E. Rhoads (2003). "Novel "anti-reverse" cap analogs with superior translational properties." *Rna-a Publication of the Rna Society* 9(9): 1108-1122.

Kabsch, W. (2010). "XDS." *Acta Crystallographica Section D—Biological Crystallography* 66: 125-132.

Kalek, M., J. Jemielity, Z. M. Darzynkiewicz, E. Bojarska, J. Stepinski, R. Stolarski, R. E. Davis and E. Darzynkiewicz (2006). "Enzymatically stable 5' mRNA cap analogs: Synthesis and binding studies with human DcpS decapping enzyme." *Bioorganic & Medicinal Chemistry* 14(9): 3223-3230.

Kalek, M., J. Jemielity, E. Grudzien, J. Zuberek, E. Bojarska, L. S. Cohen, J. Stepinski, R. Stolarski, R. E. Davis, R. E. Rhoads and E. Darzynkiewicz (2005). "Synthesis and biochemical properties of novel mRNA 5' cap analogs resistant to enzymatic hydrolysis." *Nucleosides Nucleotides & amp; Nucleic Acids* 24(5-7): 615-621.

Konarska, M. M., R. A. Padgett and P. A. Sharp (1984). "Recognition of Cap Structure in Splicing Invitro of Messenger-Rna Precursors." *Cell* 38(3): 731-736.

Kowalska, J., M. Lewdorowicz, J. Zuberek, E. Grudzien-Nogalska, E. Bojarska, J. Stepinski, R. E. Rhoads, E. Darzynkiewicz, R. E. Davis and J. Jemielity (2008). "Synthesis and characterization of mRNA cap analogs containing phosphorothioate substitutions that bind tightly to eIF4E and are resistant to the decapping pyrophosphatase DcpS." *RNA-a Publication of the RNA Society* 14(6): 1119-1131.

Kowalska, J., A. Wypijewska del Nogal, Z. M. Darzynkiewicz, J. Buck, C. Nicola, A. N. Kuhn, M. Lukaszewicz, J. Zuberek, M. Strenkowska, M. Ziemniak, M. Maciejczyk, E. Bojarska, R. E. Rhoads, E. Darzynkiewicz, U. Sahin and J. Jemielity (2014). "Synthesis, properties, and biological activity of boranophosphate analogs of the mRNA cap: versatile tools for manipulation of therapeutically relevant cap-dependent processes." *Nucleic Acids Research* 42(16): 10245-10264.

Kowalska, J., M. Ziemniak, M. Lukaszewicz, J. Zuberk, M. Strenkowska, E. Darzynkiewicz and J. Jemielity (2008). "Phosphorothioate analogs of m7GTP: Strong inhibitors of translation with increased resistance towards enzymatic degradation." *Chemistry of Nucleic Acid Components* 10: 487-490.

Kuhn, A. N., M. Diken, S. Kreiter, A. Selmi, J. Kowalska, J. Jemielity, E. Darzynkiewicz, C. Huber, O. Tureci and U. Sahin (2010). "Phosphorothioate cap analogs increase stability and translational efficiency of RNA vaccines in immature dendritic cells and induce superior immune responses in vivo." *Gene Therapy* 17(8): 961-971.

Lykke-Andersen, J. (2002). "Identification of a human decapping complex associated with hUpf proteins in nonsense-mediated decay." *Molecular and Cellular Biology* 22(23): 8114-8121.

Mccoy, A., R. Grosse-Kunstleve, P. Adams, M. Winn, L. Storoni and R. Read (2007). "Phaser crystallographic software." *Journal of Applied Crystallography* 40: 658-674.

Mildvan, A., Z. Xia, H. Azurmendi, V. Saraswat, P. Legler, M. Massiah, S. Gabelli, M. Bianchet, L. Kang and L. Amzel (2005). "Structures and mechanisms of Nudix hydrolases." *Archives of Biochemistry and Biophysics* 433(1): 129-143.

Rydzik, A. M., M. Lukaszewicz, J. Zuberek, J. Kowalska, Z. M. Darzynkiewicz, E. Darzynkiewicz and J. Jemielity (2009). "Synthetic dinucleotide mRNA cap analogs with tetraphosphate 5', 5' bridge containing methylenebis(phosphonate) modification." *Organic & Biomolecular Chemistry* 7(22): 4763-4776.

Sahin, U., K. Kariko and O. Tureci (2014). "mRNA-based therapeutics—developing a new class of drugs." *Nature Reviews Drug Discovery* 13(10): 759-780.

Schuttelkopf, A. and D. van Aalten (2004). "PRODRG: a tool for high-throughput crystallography of protein-ligand complexes." *Acta Crystallographica Section D—Biological Crystallography* 60: 1355-1363.

Shen, V., H. D. Liu, S. W. Liu, X. F. Jiao and M. Kiledjian (2008). "DcpS scavenger decapping enzyme can modulate pre-mRNA splicing." *Rna-a Publication of the Rna Society* 14(6): 1132-1142.

Singh, J., M. Salcius, S. W. Liu, B. L. Staker, R. Mishra, J. Thurmond, G. Michaud, D. R. Mattoon, J. Printen, J. Christensen, J. M. Bjornsson, B. A. Pollok, M. Kiledjian, L. Stewart, J. Jarecki and M. E. Gurney (2008). "DcpS as a Therapeutic Target for Spinal Muscular Atrophy." *Acs Chemical Biology* 3(11): 711-722.

Van Meerbeke, J. P., R. M. Gibbs, H. L. Plasterer, W. Miao, Z. Feng, M.-Y. Lin, A. A. Rucki, C. D. Wee, B. Xia, S. Sharma, V. Jacques, D. K. Li, L. Pellizzoni, J. R. Rusche, C.-P. Ko and C. J. Sumner (2013). "The DcpS inhibitor RG3039 improves motor function in SMA mice." *Human Molecular Genetics* 22(20): 4074-4083.

Warren, L., P. D. Manos, T. Ahfeldt, Y. H. Loh, H. Li, F. Lau, W. Ebina, P. K. Mandal, Z. D. Smith, A. Meissner, G. Q. Daley, A. S. Brack, J. J. Collins, C. Cowan, T. M. Schlaeger and D. J. Rossi (2010). "Highly Efficient Reprogramming to Pluripotency and Directed Differentiation of Human Cells with Synthetic Modified mRNA." *Cell Stem Cell* 7(5): 618-630.

Ziemniak, M., M. Strenkowska, J. Kowalska and J. Jemielity (2013). "Potential therapeutic applications of RNA cap analogs." *Future medicinal chemistry* 5(10): 1141-1172.

Zuberek, J., J. Jemielity, A. Niedzwiecka, J. Stepinski, A. Wyslouch-Cieszynska, R. Stolarski and E. Darzynkiewicz (2003). "Influence of the length of the phosphate chain in mRNA 5' cap analogs on their interaction with eukaryotic initiation factor 4E." *Nucleosides Nucleotides & Nucleic Acids* 22(5-8): 1707-1710.

---

The invention claimed is:

1. A 5'-phosphorothiolate cap analog according to formula 1

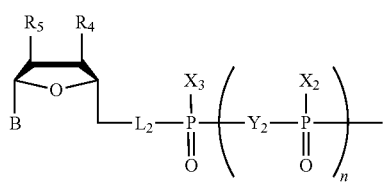

(1)

wherein $L_1$ and $L_2$ are independently selected from O or S, wherein at least one of $L_1$ and $L_2$ is not O;

n=0, 1, or 2;

$X_1$, $X_2$, and $X_3$ are independently selected from O or S;

$R_1$ is selected from $CH_3$, $C_2H_5$, $CH_2Ph$, alkyl, or substituted alkyl;

$R_2$ and $R_3$ are independently selected from H, OH, $OCH_3$, $OC_2H_5$, —COOH, $N_3$, alkyl, alkenyl or alkynyl;

$R_4$ and $R_5$ are independently selected from H, OH, $OCH_3$, $OC_2H_5$, —COOH, $CH_2COOH$, $N_3$, $CH_2N_3$, alkyl, alkenyl, or alkynyl;

$Y_1$ and $Y_2$ are independently selected from $CH_2$, CHCl, $CCl_2$, $CF_2$, CHF, NH, or O;

and B is a group according to formula 3, 4, 5, 6 or 7

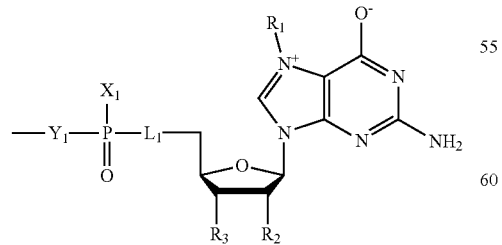

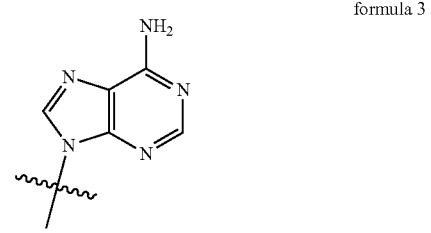

formula 3

-continued

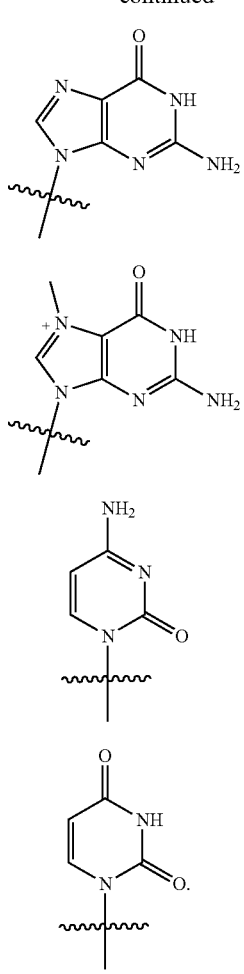

formula 4 formula 5 formula 6 formula 7

2. The 5'-phosphorothiolate cap analog according to claim 1, wherein the compound is selected from compound no. 21, 22, 23, 24, 25, 26, 30, 31, 32, 33, 34, 35, 36, 37, or 38.

3. A 5'-phosphorothiolate analog according to formula 2

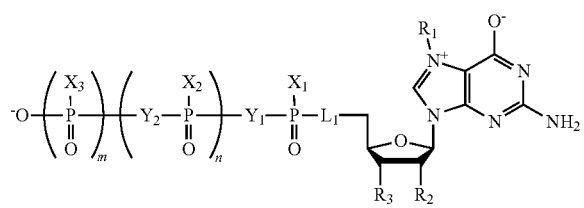
(2)

wherein
m=0 or 1;
n=0, 1, or 2;
$L_1$ is S;
$X_1$, $X_2$, and $X_3$ are independently selected from O or S;
$R_1$ is selected from $CH_3$, $C_2H_5$, $CH_2Ph$, alkyl, or substituted alkyl;
$R_2$ and $R_3$ are independently selected from H, OH, $OCH_3$, $OC_2H_5$, —COOH, $N_3$, alkyl, or substituted alkyl; and
$Y_1$ and $Y_2$ are independently selected from $CH_2$, CHCl, $CCl_2$, CHF, $CF_2$, NH, or O.

4. A method for treating a disease or symptoms of a disease comprising administering the 5'-phosphorothiolate cap analog of claim 1.

5. The method of claim 4, wherein the disease or symptoms of a disease is spinal muscular atrophy (SMA) or a symptom of SMA.

6. A composition comprising the 5'-phosphorothiolate cap analog of claim 1.

7. A method for treating spinal muscular atrophy (SMA) or symptoms of SMA, comprising administering the composition of claim 6.

8. A method for regulating DcpS activity, inhibiting of DcpS enzyme activity, or inhibiting hDcpS enzyme activity comprising contacting the 5'-phosphorothiolate cap analog of claim 1.

9. A method for regulating mRNA degradation, mRNA splicing, or both, comprising contacting the 5'-phosphorothiolate cap analog of claim 1.

10. A pharmaceutical formulation comprising the 5'-phosphorothiolate cap analog according to claim 1 and a pharmaceutically acceptable carrier.

11. An mRNA comprising at the 5' end the 5'-phosphorothiolate cap analog according to claim 1.

12. The mRNA according to claim 11, wherein said 5'-phosphorothiolate cap analog is selected from a group consisting of $m^7$GSpppG (no. 24), $m^{7,2'O}$GSpppG (no. 26), $m^7$GSpppSG (no. 32), $m^7$GSpp$_s$pG D1 (no. 30), $m^7$GSpp$_s$pG D2 (no. 31), $m^7$GSpp$_s$pSG D1 (no. 33), and $m^7$GSpp$_s$pSG D2 (no. 34).

13. A method of preparation of mRNA comprising at the 5' end of the mRNA molecule a 5'-phosphorothiolate cap analog, characterized in that the 5'-phosphorothiolate cap analog of claim 1 is incorporated during synthesis of the mRNA molecule.

14. The method of preparation of mRNA according to claim 13, characterized in that the 5'-phosphorothiolate cap analog is selected from a group comprising $m^7$GSpppG (no. 24), $m^{7,2'O}$GSpppG (no. 26), $m^7$GSpppSG (no. 32), $m^7$GSpp$_s$pG D1 (no. 30), $m^7$GSpp$_s$pG D2 (no. 31), $m^7$GSpp$_s$pSG D1 (no. 33), $m^7$GSpp$_s$pSG D2 (no. 34), more preferably it is $m^{7,2'O}$GSpppG (no. 26).

15. The method of preparation of mRNA according to claim 13 characterized in that the synthesis of mRNA proceeds through transcription in vitro.

16. An mRNA prepared with the method according to claim 13.

17. A method for the production of proteins using mRNA comprising the 5'-phosphorothiolate cap analog according to claim 11.

18. The method according to claim 17, characterized in that the production of proteins carried out in a cellular or a non-cellular system.

19. A method for treating a disease or symptoms of a disease comprising administering mRNA according to claim 11.

20. The method for treating a disease or symptoms of a disease according to claim 19, wherein the treatment is of spinal muscular atrophy (SMA) an/or for alleviation of symptoms of SMA.

21. The method for treating a disease or symptoms of a disease according to claim 19, wherein the disease is cancer.

22. A composition comprising the mRNA according to claim 11.

23. The composition of claim 22, wherein the composition is for treatment of spinal muscular atrophy (SMA), for alleviation of symptoms of SMA, for use as an anti-cancer medicament, or for use in an anti-cancer immunotherapy.

24. A pharmaceutical formulation comprising the mRNA according to claim 11 and a pharmaceutically acceptable carrier.

\* \* \* \* \*